(12) United States Patent
Kawamura et al.

(10) Patent No.: US 6,509,482 B2
(45) Date of Patent: Jan. 21, 2003

(54) OPTICALLY ACTIVE 1,4-BENZODIOXIN-2-CARBOXYLIC ACID DERIVATIVES AND PROCESS FOR PRODUCING THE SAME

(75) Inventors: Koji Kawamura, Saitama-ken (JP); Masahiro Ueno, Saitama-ken (JP); Masashi Suzuki, Saitama-ken (JP); Makoto Yanai, Saitama-ken (JP); Toshihiro Takahashi, Saitama-ken (JP); Koichi Itoh, Saitama-ken (JP)

(73) Assignee: Nisshin Pharma Inc., Tokyo (JP)

( * ) Notice: Subject to any disclaimer, the term of this patent is extended or adjusted under 35 U.S.C. 154(b) by 0 days.

(21) Appl. No.: 09/978,690

(22) Filed: Oct. 18, 2001

(65) Prior Publication Data

US 2002/0028957 A1 Mar. 7, 2002

Related U.S. Application Data

(62) Division of application No. 09/765,424, filed on Jan. 22, 2001, now Pat. No. 6,329,533, which is a division of application No. 09/509,200, filed as application No. PCT/JP99/03963 on Jul. 23, 1999, now Pat. No. 6,222,050.

(30) Foreign Application Priority Data

Jul. 31, 1998 (JP) .......................................... 10-217829

(51) Int. Cl.[7] ............................................ C07D 319/14
(52) U.S. Cl. ...................................................... 549/366
(58) Field of Search ................................. 549/366, 362

(56) References Cited

U.S. PATENT DOCUMENTS 5,482,971 A * 1/1996 Epstein et al. ............... 514/465
6,222,050 B1 * 4/2001 Kawamura et al. .......... 549/366
6,329,533 B2 * 12/2001 Kawamura et al. .......... 549/366

FOREIGN PATENT DOCUMENTS

| EP | 18675 | 11/1980 |
|---|---|---|
| JP | 6-329665 | 11/1994 |
| JP | 11-140079 | 5/1999 |
| WO | 96/35685 | 11/1996 |
| WO | 98/29405 | 7/1998 |

OTHER PUBLICATIONS

"A New Method for the Conversion of Optically Active Alcohols to Halides with Inversion of Configuration", by Stevens, et al., J. Am. Chem. Soc., vol. 77, 1955, 2341–2342.
"Preparation of Alkyl Bromides from the Corresponding Alcohols and Me$_2$SBr$_2$", by Furukawa et al., J. C. S. Chem. Commun, 1973, pp. 212–213.
"Synthesis of Alkyl Halides Under Neutral Conditions", by Munyemana, et al., Tetrahedron Letters vol. 30, No. 23, 1989, pp. 3077–3080.
"Synthesis of Optically Active Alkyl Halides", by Hudson, Synthesis, 1969, pp. 112–119.
"Studies in Organo–Phosphorus Chemistry. II. Mechanism of the Reaction of Tertiary Phosphine Dihalides with Alcohols", by Wiley et al, Tetrahedron Letters No. 36, 1964, pp. 2509–2513.
"A Rapid, Mild Procedure for the Preparation of Alkyl Chlorides and Bromides", by Hooz et al., Canadian Journal of Chemistry, vol. 46, 1968, pp. 86–87.
"Acyl Amides as Epimerization Reagents", by Chang et al., Journal of American Chemical Society, vol. 80, 1958, pp. 2906.
"Stereochemistry of Acetolysis of Alkyl Sulfonates", by Streitwieser, Jr. et al., Journal of the American Chemical Society, Vo. 87, No. 16, Aug. 20, 1965, pp. 3682–3685.
"Salt Effects in the Stereochemistry of Acetolysis of 2–Octyl ρ–Toluenesulfonate", by Steitwieser et al., Journal of American Chemical Society, vol. 87, No. 16, Aug. 20, 1965, pp. 3686–3691.
"New Method for the Preparation of Unsaturated Axial 3–Sterols", by Baker et al., J. Chem. Soc. (C), 1969, pp. 1605–1606.
"Optical Interconversion of Enantiomeric Secondary Alcohols using 2–Fluorobenzothiazolium Salt", by Mukaiyama et al., Chemistry Letters, 1976, pp. 893–896.
"The Role of Neighboring Groups in Replacement Reactions. I. Retention of Configuration in the Reaction of Some Dihalides and Acetoxyhalides and Silver Acetate", by Winstein et al., J. Am. Chem. Soc., vol. 64, 1942, pp. 2780–2786.

* cited by examiner

*Primary Examiner*—Deborah C. Lambkin
*Assistant Examiner*—Ebenezer Sackey
(74) *Attorney, Agent, or Firm*—McDermott, Will & Emery

(57) ABSTRACT

Disclosed are optically active alcohols having formulae (1) and (2)

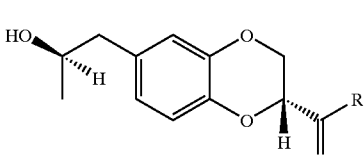

(1)

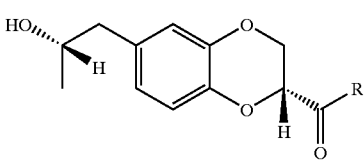

(2)

wherein R is (R)-1-phenylethylamino or (S)-1-phenylethylamino.

1 Claim, No Drawings

OPTICALLY ACTIVE 1,4-BENZODIOXIN-2-CARBOXYLIC ACID DERIVATIVES AND PROCESS FOR PRODUCING THE SAME

This application is a division of 09/765,424 filed Jan. 22, 2001 now U.S. Pat. No. 6,329,533 which is a division of 09/509,200 filed Mar. 23, 2000 now U.S. Pat. No. 6,222,050 which is a 371 of PCT/JP99/03963 filed Jul. 23, 1999.

1. Field of The Invention

The present invention relates to optically active 1,4-benzodioxin-2-carboxylic acid derivatives which are intermediates useful for the synthesis of (RRR)-optical isomers of 1,4-benzodioxin-2-carboxylic acid derivatives which are useful as a prophylactic and therapeutic agent for diabetes, hyperglycemia and the like, and processes for the preparation thereof. The invention also relates to processes for effectively preparing (RRR)-optical isomers of 1,4-benzodioxin-2-carboxylic acid derivatives using these intermediates.

2. Background Art

WO 96/35685 discloses an (RRR)-optical isomer of 1,4-benzodioxin-2-carboxylic acid derivatives represented by the following general formula (7') which is useful as a prophylactic and therapeutic agent for diabetes, hyperglycemia and the like, and a process for the preparation thereof.

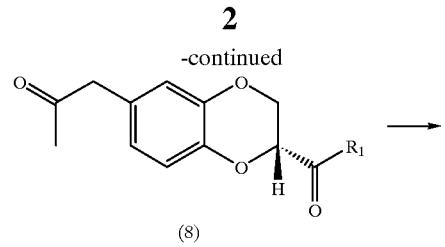

(7')

wherein $R_1$ is hydroxy or $(C_1-C_4)$alkoxy, and $R_2$ and $R_3$ may be the same or different, and each is hydrogen, halogen, $(C_1-C_6)$alkyl, trifluoromethyl, $(C_1-C_6)$alkoxy, aryl, aryloxy or aryl$(C_1-C_6)$alkyloxy, the aryl, aryloxy or aryl$(C_1-C_6)$alkyloxy being optionally substituted by one or two halogens, or $R_2$ and $R_3$ may together form —$OCH_2O$—.

According to a method disclosed in WO 96/35685, a compound of the above formula (7') is prepared as shown in the following Scheme I. A compound of formula (6) is reductively condensed with a compound of formula (8) to form a mixture of diastereoisomers of formula (9), which is then converted into an N-tert-butoxy carbonyl derivative of formula (10), and the derivative is separated into diastereoisomers of formulae (11) and (12) by column chromatography, and then a compound of formula (11) is hydrolyzed to prepare an (RRR)-optical isomer of 1,4-benzodioxin-2-carboxylic acid derivatives represented by the formula (7').

Scheme I

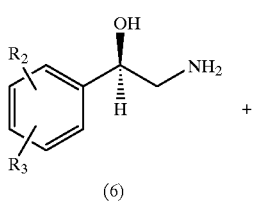

(6)

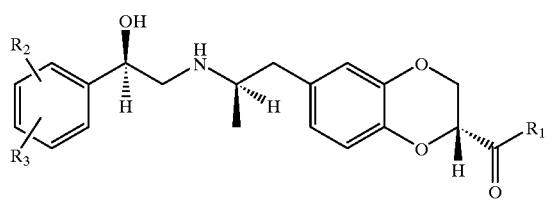

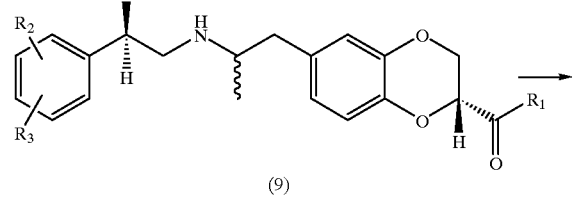

(8)

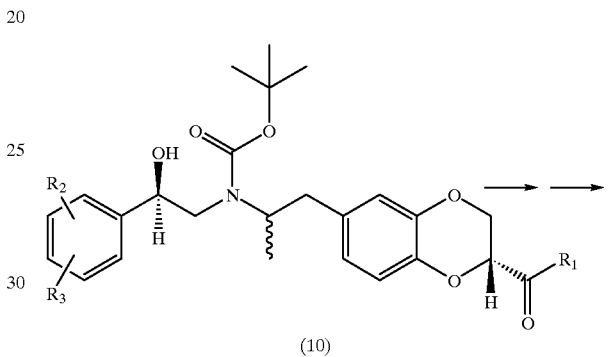

(9)

(10)

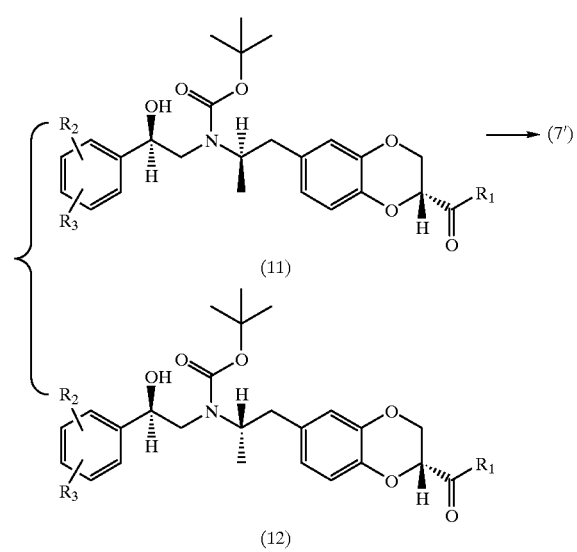

(11)

(12)

The above-mentioned process has not been accepted as an efficient method, because it forms a compound of formula (12) which is not required for the production of a desired compound [formula (7')], which resulted in reducing a total yield of the desired compound.

Therefore, it has been demanded to efficiently produce an (RRR)-optical isomer of 1,4-benzodioxin-2-carboxylic acid derivatives represented by the formula (7'), which is useful as a prophylactic and therapeutic agent for diabetes, hyperglycemia and the like.

DISCLOSURE OF THE INVENTION

In view of the above-mentioned problems, the present inventors have zealously studied a process for producing efficiently a compound of formula (7'). As a result, the inventors have succeeded in producing the desired compound in high yield with the reduced formation of unnecessary optical isomers and not accompanied by complicated steps. The present invention is based on findings that optically active alcohols of the following formulae (1) and (2) are useful as starting materials, which can be obtained by acylating racemates of the following formula (3) in the presence of a hydrolase, followed by separation, and also that the desired 1,4-benzodioxin-2-carboxylic acid derivative represented by the above formula (7') can be produced very efficiently and more selectively via an intermediate of the following formula (7) which can be obtained by condensing an optically active halogenated product or sulfonylated product (a compound of the following formula (5)) obtained by halogenating or sulfonylating these starting materials with an (R)-2-amino-1-phenylethanol derivative (a compound of the following formula (6)).

According to the present invention, a mixture of a compound of formula (2)

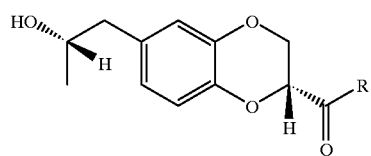

(2)

wherein R is as defined below and a compound of formula (4)

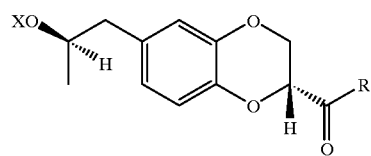

(4)

wherein R is as defined below and X is $(C_1–C_4)$acyl can be obtained by reacting a racemate of formula (3)

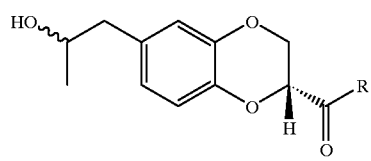

(3)

wherein R is (R)-1-phenylethylamino or (S)-1-phenylethylamino with an acylating agent in the presence of a hydrolase. Separating the resultant mixture can provide each compound with high optical purity and in high yield. Further, the compound of formula (4) obtained above can be easily converted by hydrolysis or alcoholysis into a compound of formula (1)

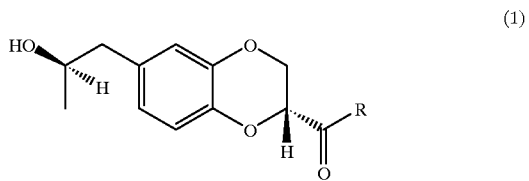

(1)

wherein R is as defined above.

Further, a compound of formula (7) (which is an intermediate of formula (7')),

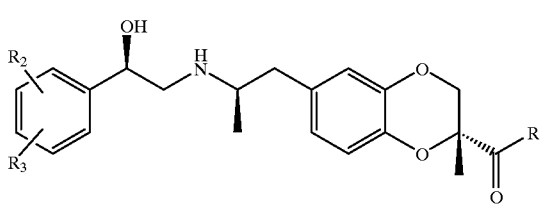

(7)

wherein R is as defined above, and $R_2$ and $R_3$ may be the same or different and each is hydrogen, halogen, $(C_1–C_6)$alkyl, trifluoromethyl, $(C_1–C_6)$alkoxy, aryl, aryloxy or aryl$(C_1–C_6)$alkyloxy, the aryl, aryloxy or aryl$(C_1–C_6)$alkyloxy being optionally substituted by one or two halogen atoms, or $R_2$ and $R_3$ together may form —$OCH_2O$—, can be prepared from the compound of formula (1) or (2) easily and in high yield.

The present invention thus provides the compound of formula (1)

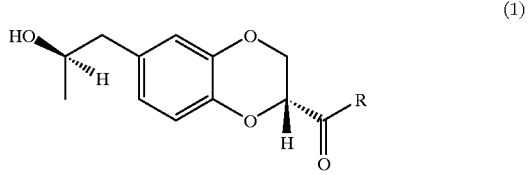

(1)

wherein R is (R)-1-phenylethylamino or (S)-1-phenylethylamino.

The invention also provides the compound of formula (2)

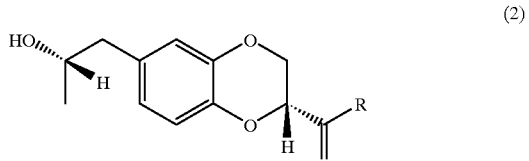

(2)

wherein R is (R)-1-phenylethylamino or (S)-1-phenylethylamino.

Further, the present invention provides a process for preparing the compound of formula (1)

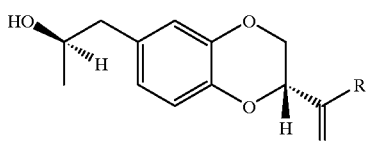
(1)

wherein R is as defined above and the compound of formula (2)

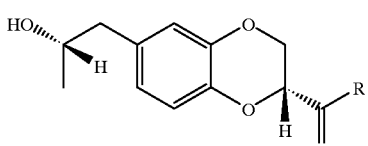
(2)

wherein R is as defined above, which comprises the steps of: reacting the racemate of formula (3)

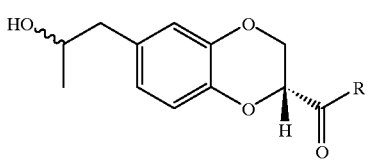
(3)

wherein R is (R)-1-phenylethylamino or (S)-1-phenylethylamino with an acylating agent in the presence of a hydrolase to give the compound of formula (4)

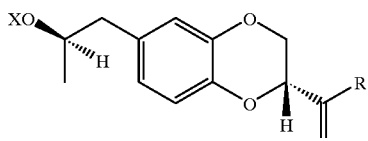
(4)

wherein R is as defined above and X is $(C_1-C_4)$acyl and the compound of formula (2)

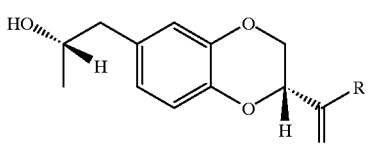
(2)

wherein R is as defined above, followed by separation, and subjecting the compound of formula (4) to alcoholysis or hydrolysis.

Further, the invention provides a process for preparing the compound of formula (7)

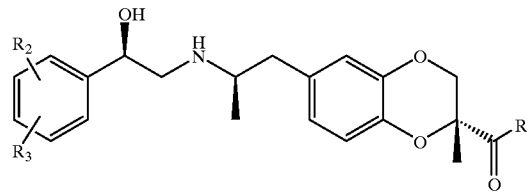
(7)

wherein R, $R_2$ and $R_3$ are as defined below, which comprises the steps of:
reacting the compound of formula (1)

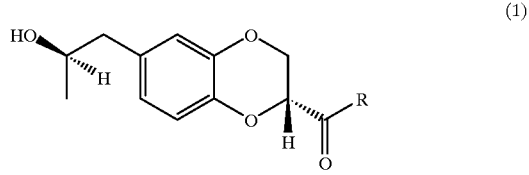
(1)

wherein R is (R)-1-phenylethylamino or (S)-1-phenylethylamino or the compound of formula (2)

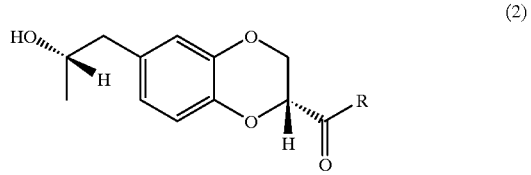
(2)

wherein R is (R)-1-phenylethylamino or (S)-1-phenyl-ethylamino with a halogenating agent or a sulfonylating agent, and condensing the resulting compound of formula (5)

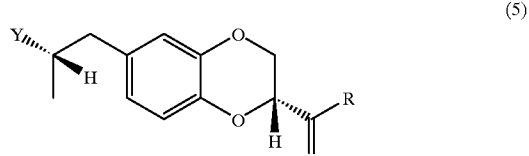
(5)

wherein R is as defined above and Y is halogen, $(C_1-C_4)$ alkylsulfonyloxy or arylsulfonyloxy with the compound of formula (6)

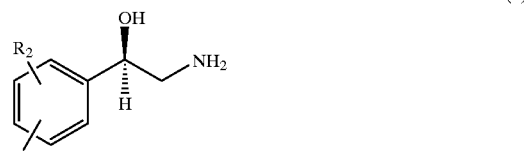
(6)

wherein $R_2$ and $R_3$ may be the same or different, and each is hydrogen, halogen, $(C_1-C_6)$alkyl, trifluoromethyl, $(C_1-C_6)$alkoxy, aryl, aryloxy or aryl$(C_1-C_6)$alkyloxy, the aryl, aryloxy or aryl$(C_1-C_6)$alkyloxy being optionally substituted by one or two halogen atoms, or $R_2$ and $R_3$ together may form —$OCH_2O$—.

The compounds of formulae (1) and (2) are very useful as starting materials for the compound of formula (7') which is useful as medicines and the compound of formula (7) which is an intermediate for the compound of formula (7').

Specific examples of the compounds of formulae (1) and (2) include 6-(2-(R)-hydroxypropyl)-2,3-dihydro-1,4-benzodioxin-(N-(1-(S)-phenylethyl))-2-(R)-carboxamide, 6-(2-(R)-hydroxypropyl)-2,3-dihydro-1,4-benzodioxin-(N-(1-(R)-phenylethyl))-2-(R)-carboxamide, 6-(2-(S)-hydroxypropyl)-2,3-dihydro-1,4-benzodioxin-(N-(1-(R)-phenylethyl))-2-(R)-carboxamide, and 6-(2-(S)-hydroxypropyl)-2,3-dihydro-1,4-benzodioxin-(N-(1-(S)-phenylethyl))-2-(R)-carboxamide.

As shown in the following Scheme II, the racemate of formula (3) is reacted with an acylating agent in the presence of a hydrolase to produce a mixture of the compound of formula (2) and the compound of formula (4).

Scheme II

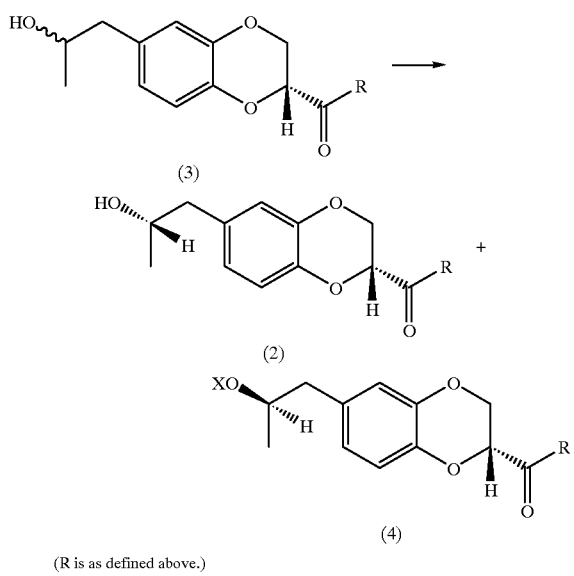

(R is as defined above.)

Such a mixture can be separated into each compound by any of known separation methods based on differences in physical and chemical properties of each compound. These separation methods include fractional crystallization, fractional distillation, chromatography, fractional extraction and the like.

In formula (4), X represents a ($C_1$–$C_4$)acyl group, examples of which can include acetyl, propionyl, n-butyryl and isobutyryl.

Hydrolases which can be used in the present invention include lipase or esterase, specific examples of which include Candida cylindrarea (trade name "Ald. Type III Lipase", manufactured by Aldrich), Pseudomonas cepacia (trade name "Lipase PS", manufactured by Amano pharmaceutical Co., Ltd.), Pseudomonas aeruginosa (trade name "DLIP-300", manufactured by Toyobo), Pseudomonas fluorescence (trade name "Lipase AK", manufactured by Amano pharmaceutical Co., Ltd.), Aspergillus niger (trade name "Lipase A-6", manufactured by Amano pharmaceutical Co., Ltd.), Rhizopus oryzae (trade name "Lipase F-AP-15", manufactured by Amano pharmaceutical Co., Ltd.), Candida cylindracea (trade name "Lipase AY", manufactured by Amano pharmaceutical Co., Ltd.), Candida rugosa (trade name "Sigma type VII Lipase", manufactured by Sigma), Mucor javanicus (trade name "Lipase M", manufactured by Amano pharmaceutical Co., Ltd.), Porcine Pancreas Lipase (trade name "Sigma type II Lipase", manufactured by Sigma), Porcine Liver Esterase (manufactured by Sigma). Pseudomonas fluorescence (trade name "Lipase AK", manufactured by Amano pharmaceutical Co., LTD.) or Pseudomonas cepacia (trade name "Lipase PS", manufactured by Amano pharmaceutical Co., Ltd.) are particularly preferable.

An acylating agent used in the present method includes lower fatty acid anhydrides such as acetic anhydride, propionic anhydride and the like, and lower carboxylic esters such as methyl acetate, vinyl acetate, isopropenyl acetate, isopropenyl propionate, isopropenyl butyrate and the like. Preferred acylating agents are those which do not cause by-products produced by elimination of an acyl group to react reversibly when used in acylation, for example, vinyl acetate, isopropenyl acetate and the like, which are converted into acetaldehyde, acetone and the like. The acylating agent is used in propotion of 1–50 equivalent weights, preferably 3–20 equivalent weights.

Acylation can be carried out without any solvents, i.e., by using an acylating agent per se as a solvent, but in view of easiness in reaction processes, it is preferably carried out in the presence of a solvent. The solvents employed are not specifically limited unless giving any influence on the reaction, which can include hydrocarbons such as pentane, hexane, benzene, toluene, xylene and the like; halogenated hydrocarbons such as dichloromethane, chloroform, carbon tetrachloride and the like; ethers such as diethyl ether, diisopropyl ether, t-butyl methyl ether, tetrahydrofuran, dioxane and the like; and ketones such as acetone, methyl ethyl ketone and the like, which are used alone or in combination.

The reaction time depends on kinds and amounts of hydrolases used and reaction temperature, but it ranges from one hour to 10 days. The reaction temperature ranges from room temperature to 40° C., at which temperature the deactivation of hydrolases does not occur, and the reaction is preferably performed at the optimum temperature of the hydrolase used.

Separating operation following the acylation is carried out by chromatography, fractional crystallization, fractional extraction or by a combination thereof.

Column carriers employed in chromatography can include, e.g., silica gel, and a mobile phase employed is not specifically limited, unless giving any influence on the separation, which can include hydrocarbons such as benzene, toluene, xylene, hexane, heptane and the like; halogenated hydrocarbons such as chloroform, methylene chloride, carbon tetrachloride and the like; ethers such as diethyl ether, diisopropyl ether, tetrahydrofuran and the like; alcohols such as methanol, ethanol, isopropanol and the like; acetic acid esters such as ethyl acetate, methyl acetate and the like; ketones such as acetone, methyl ethyl ketone and the like, or a mixed solvent of these, preferably mixed solvents of acetic acid esters or ketons with hydrocarbons, in particular, mixed solvents of ethyl acetate with hexane or acetone with toluene.

Solvents employed in fractional crystallization are not specifically limited, unless giving any influence on the recrystallization, which can include hydrocarbons such as benzene, toluene, xylene, hexane, heptane and the like; halogenated hydrocarbons such as chloroform, methylene chloride, carbon tetrachloride and the like; ethers such as diethyl ether, diisopropyl ether, tetrahydrofuran and the like; alcohols such as methanol, ethanol, isopropanol and the like; acetic acid esters such as ethyl acetate, methyl acetate and the like; ketones such as acetone, methyl ethyl ketone and the like, or a mixed solvent of these, preferably hydrocarbons, a mixed solvent of acetic acid esters and hydrocarbons or a mixed solvent of ethers and hydrocarbons, more preferably xylene, toluene or a mixed solvent of diisopropyl ether and xylene (mixing ratio 1:99–99:1, v/v). Recrystallization temperature varies depending on the conditions of solvents and the like, and usually ranges from 0° C. to reflux temperature of the solvent used, preferably from 0° C. to room temperature.

Solvents employed in fractional extraction are not specifically limited, unless giving any influence on the separation, which can include hydrocarbons such as benzene, toluene, xylene, hexane, heptane and the like; halogenated hydrocarbons such as chloroform, methylene chloride, carbon tetrachloride and the like; ethers such as diethyl ether, diisopropyl ether, tetrahydrofuran and the like; alcohols such as methanol, ethanol, isopropanol and the like; acetic acid esters such as ethyl acetate, methyl acetate and the like; ketones such as acetone, methyl ethyl ketone and the like; amides such as dimethylformamide and the like; sulfoxides such as dimethylsulfoxide and the like; water or a mixed solvent of these, preferably a mixed solvent of hydrocarbons, alcohols and water.

The compound of formula (2) thus prepared is used as it is as a starting material of the compound of formula (7), while the compound of formula (4) is converted by hydrolysis or alcoholysis into the compound of formula (1) which is another important starting material.

Acids used for hydrolysis of the compound of formula (4) can include inorganic acids such as hydrochloric acid, sulfuric acid and the like; organic acids such as acetic acid, methanesulfonic acid, toluenesulfonic acid and the like.

Bases used for hydrolysis or alcoholysis can include carbonates such as sodium carbonate, potassium carbonate, sodium hydrogencarbonate, potassium hydrogencarbonate and the like; alkali metal hydroxides such as sodium hydroxide, potassium hydroxide and the like; organic bases such as trimethylamine, triethylamine, diisopropylamine, diisopropylethylamine, pyridine, quinoline and the like. The acids or bases can be used in an amount ranging from a catalytic amount to an excess amount, and 0.1–10 equivalent weights of carbonates or alkali metal hydroxides may preferably be used.

The hydrolysis is preferably carried out in the presence of solvents in view of easiness in reaction processes. Examples of solvents can include alcohols such as methanol, ethanol, isopropanol and the like; ketones such as acetone, methyl ethyl ketone and the like; ethers such as diethyl ether, diisopropyl ether, tetrahydrofuran, dioxane and the like; and water. Mixed solvents of alcohols and water are preferred. The reaction temperature ranges from 0° C. to reflux temperature of solvents employed, preferably from 0° C. to room temperature. The reaction time ranges from one minute to 72 hours.

As shown in Scheme III, the compounds of formulae (1) and (2) thus prepared can be respectively converted into the compound of formula (5) by halogenation or sulfonylation, followed by condensation with the compound of formula (6), thus leading to the compound of formula (7).

Scheme III

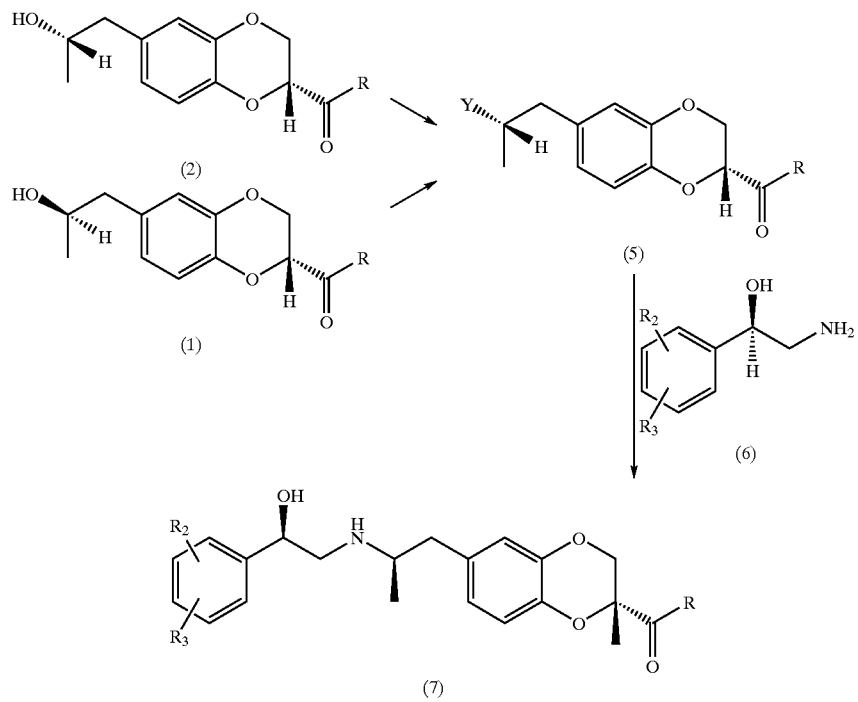

Examples of halogen represented by Y in the compound of formula (5) can include fluorine, chlorine, bromine and iodine. Examples of $(C_1-C_4)$alkylsulfonyloxy can include methanesulfonyloxy, ethanesulfonyloxy, n-propylsulfonyloxy, isopropylsulfonyloxy and n-butylsulfonyloxy. Examples of arylsulfonyloxy can include benzenesulfonyloxy and p-toluenesulfonyloxy.

The compound of formula (1) and the compound of formula (2) are respectively halogenated or sulfonylated, with inversion of configuration for said compound (1) and with retention of configuration for said compound (2), thereby converting into the compound of formula (5).

The halogenating agent used in halogenation with inversion of configuration can include, for example, acetonitrile and hydrochloric acid (J. Am. Chem. Soc., Vol. 77, 2341, (1955)), dimethylbromosulfonium bromide (J. C. S. Chem. Commun., 212–213, (1973)), tetramethyl α-haloenamine (Tetrahedron Lett., Vol. 30, 3077–3080, (1989)), phosphorus tribromide and phosphorus pentachloride (Synthesis, 1969, 112), triphenylphosphine and carbon tetrahalide such as carbon tetrachloride and carbon tetrabromide or triphenylphosphine dihalide (Tetrahedron Lett., 2509, (1964), Canad. J. Chem., Vol. 46, 86, (1968)) and the like.

The halogenation using triphenylphosphine and carbon tetrahalide, or triphenylphosphine and bromine or iodine is preferable. Triphenylphosphine is used in the amount of 1–10 equivalent weights and carbon tetrahalide or bromine or iodine is used in the amount of 1–10 equivalent weights. The reaction solvents can include halogenated hydrocarbons such as methylene chloride, chloroform, dichloroethane, trichloroethane and the like; ethers such as dimethyl ether, diethyl ether, diisopropyl ether, t-butyl methyl ether, tetrahydrofuran, dioxane and the like; hydrocarbons such as pentane, hexane, heptane, benzene, toluene, xylene and the like. Halogenated hydrocarbons such as methylene chloride are preferable. The reaction temperature ranges from 0° C. to reflux temperature of solvents used, preferably from 0° C. to room temperature. The reaction time ranges from one minute to 10 hours.

The compound of formula (2) can be converted into the compound of formula (5) with retention of configuration by halogenation with a halogenating agent-such as thionyl chloride, thionyl bromide and the like or by sulfonylation with a sulfonylating agent such as $(C_1-C_4)$alkylsulfonyl halides, arylsulfonyl halides and the like.

For the halogenation of the compound of formula (2), halogenating agents such as thionyl chloride, thionyl bromide and the like are used in the amount ranging from one equivalent weight to large excess amount. The reaction can be carried out in the presence or absence of solvents, for example, hydrocarbons such as pentane, hexane, heptane, benzene, toluene, xylene and the like; halogenated hydrocarbons such as methylene chloride, chloroform, carbon tetrachloride, dichloroethane, trichloroethane and the like. Organic bases such as pyridine, quinoline, triethylamine and the like, unless giving any influence on the configuration of a reaction product, may also be used concurrently. The reaction temperature ranges from –20° C. to reflux temperature of the solvents used. The reaction time depends on the reagents and solvents used, and usually ranges from one minute to 10 hours.

For the conversion of the compound of formula (2) into the compound of formula (5) in which Y is $(C_1-C_4)$ alkylsulfonyloxy or arylsulfonyloxy, $(C_1-C_4)$alkylsulfonyl halides such as methanesulfonyl chloride, ethanesulfonyl chloride and the like and arylsulfonyl halides such as benzenesulfonyl chloride, p-toluenesulfonyl chloride and the like can be used. The solvents used are not specifically limited unless giving any influence on reaction, which can include ethers such as dimethyl ether, diethyl ether, diisopropyl ether, t-butyl methyl ether, tetrahydrofuran, dioxane and the like; polar solvents such as dimethylformamide, dimethylacetamide, dimethylsulfoxide and the like; hydrocarbons such as pentane, hexane, heptane, benzene, toluene, xylene and the like; halogenated hydrocarbons such as methylene chloride, chloroform, carbon tetrachloride, dichloroethane, trichloroethane and the like. Organic bases such as triethylamine, pyridine, dimethylaminopyridine, quinoline and the like may also be used concurrently. The reaction can be carried out at the temperature ranging from 0° C. to reflux temperature of the solvent used, preferably from 0° C. to room temperature.

As described above, either of the compound of formula (1) or the compound of formula (2), whose configuration is different each other, can be converted by halogenation or sulfonylation into the same compound, i.e., the compound of formula (5). Converting each of the compounds of formulae (1) and (2) into the compound of formula (5) makes both the compounds available as a material for preparing the compound of formula (7) and also it advantageously makes subsequent production steps simplified, thereby obtaining the desired compound efficiently in high yield.

Alternatively, the optically active alcohol of formula (1) is allowed to sterically invert to the optically active alcohol of formula (2), or the optically active alcohol of formula (2) can be converted into the optically active alcohol of formula (1).

In general, the methods for the inversion of configuration of the optically active alcohol can include a method wherein an optically active alcohol is converted into its sulfonic acid ester which is then reacted with dimethylformamide (J. Am. Chem. Soc., Vol. 80, 2906, (1958)), a method wherein an optically active alcohol is converted into its sulfonic acid ester which is then reacted with acetic acid (J. Am. Chem. Soc., Vol. 87, 3682, (1965), J. Am. Chem. Soc., Vol. 87, 3686, (1965)), a method wherein an optically active alcohol is converted into its sulfonic acid ester which is then reacted with tetraalkylammonium acetate (J. Chem. Soc. (c), 1969, 1605–1606), and a method wherein an optically active alcohol is led to its alkoxybenzothiazorinium which is then reacted with trichloroacetic acid (Chem. Lett., 1976, 893–896) and so on. A sterically inverted optically active alcohol can also be obtained by reaction with silver acetate (J. Am. Chem. Soc., Vol. 64, 2780 (1942)) following the halogenation with inversion of configuration as discussed above.

For instance, the above method of converting an optically active alcohol into its sulfonic acid ester followed by reacting with dimethylformamide is accomplished by using one equivalent weight to a large excess of dimethylformamide after the conversion of the optically active alcohol into the sulfonic acid ester thereof. The solvents used are not specifically limited unless giving any influence on the reaction, which can include hydrocarbons such as benzene, toluene, xylene, hexane, heptane and the like; halogenated hydrocarbons such as chloroform, methylene chloride, carbon tetrachloride and the like; ethers such as diethyl ether, diisopropyl ether, tetrahydrofuran and the like; alcohols such as methanol, ethanol, isopropanol and the like; acetic acid esters such as ethyl acetate, methyl acetate and the like; ketones such as acetone, methyl ethyl ketone and the like; sulfoxides such as dimethylsulfoxide and the like; and water or a mixture of these. Dimethylformamide per se can be used. The reaction is carried out at any temperature ranging from 0° C. to reflux temperature of the solvents used. The reaction time is from 3 hours to 6 days, depending on solvents and reaction temperature and so on. Preferably, the reaction is carried out at a temperature ranging from 50° C. to reflux temperature of the solvent for 3 to 72 hours, using ketones such as methyl ethyl ketone and the like, sulfoxides such as dimethylsulfoxide and the like, or dimethylformamide per se.

After an intensive conversion into the compound of either formula (1) or (2) in the above manner, it is also possible to subject each compound to the above halogenation or sulfonylation, thereby leading to the compound of formula (5).

The compound of formula (5) obtained as described above is condensed with the compound of formula (6) into the compound of formula (7).

This condensation reaction is carried out by using 1 to 20 equivalent weights of the compound of formula (6) in the absence or presence of solvents. The solvents which may be used include ethers such as dimethyl ether, diethyl ether, diisopropyl ether, t-butyl methyl ether, tetrahydrofuran, dioxane and the like; aprotic polar solvents such as dimethylformamide, dimethylacetamide, dimethylsulfoxide and the like; hydrocarbons such as pentane, hexane, heptane, benzene, toluene, xylene, and the like; and halogenated hydrocarbons such as methylene chloride, chloroform, carbon tetrachloride dichloroethane, trichloroethane and the like. The reaction can be carried out in the presence of bases such as organic bases, for example, triethylamine, pyridine, quinoline and the like, or inorganic bases, for example, sodium hydrogencarbonate, potassium hydrogencarbonate, sodium carbonate, potassium carbonate, sodium hydroxide, potassium hydroxide and the like. The reaction temperature ranges from room temperature to reflux temperature of the solvent used. The reaction time ranges from one hour to 72 hours.

The compound of formula (7) thus obtained can be converted by hydrolysis into a compound of formula (7') wherein $R_1$ is a hydroxy group, which is a useful end product as medicines as described above. The hydrolysis can be carried out using inorganic bases such as sodium hydroxide, potassium hydroxide, sodium carbonate, potassium carbonate and the like, or inorganic acids such as sulfuric acid, hydrochloric acid and the like. The solvents used can include water; alcohols such as methanol, ethanol, isopropanol, butanol, t-butyl alcohol and the like; organic acids such as formic acid, acetic acid, propionic acid and the like; and a mixture thereof. The reaction temperature ranges from room temperature to reflux temperature of the solvent used. The reaction time ranges from 10 minutes to 72 hours.

Further, the compound of formula (7') wherein $R_1$ is a hydroxy group may be esterified and isolated as a compound of formula (7') wherein $R_1$ is a $(C_1-C_4)$alkoxy group, without isolation as the carboxylic acid after hydrolysis of the compound of formula (7). More specifically, an ester compound of formula (7') can easily be prepared by distilling off the solvent under reduced pressure after completion of hydrolysis of the compound of formula (7), adding to the residue $(C_1-C_4)$alcohols such as methanol, ethanol, propanol and the like, and then esterifying under acidic conditions. The acids used can include usual inorganic acids such as hydrochloric acid, sulfuric acid and the like. The reaction temperature ranges from 0° C. to reflux temperature of the alcohol used. The reaction time ranges from one minute to 10 hours.

Further, the compound of formula (7') wherein $R_1$ is a $(C_1-C_4)$alkoxy group can be again and easily converted by hydrolysis into the compound of formula (7') wherein $R_1$ is a hydroxy group.

The hydrolysis can be carried out by using inorganic bases such as sodium hydroxide, potassium hydroxide, sodium carbonate, potassium carbonate, sodium hydrogencarbonate, potassium hydrogencarbonate and the like or inorganic acids such as hydrochloric acid, sulfuric acid and the like, in water or in a mixed solution of water and solvents, for example, alcohols such as methanol, ethanol, propanol, butanol and the like, acetonitrile, propionitrile, tetrahydrofuran, dioxane and the like. The reaction is carried out at a temperature ranging from room temperature to reflux temperature and completed in 10 minutes to 10 hours.

Racemates of formula (3) used as a starting material in the present invention can be synthesized as shown in the following scheme IV, starting from a compound of formula (13), via a compound of formula (15) condensed with nitroethane and reducing a compound of formula (8') in accordance with the process described in WO 96/35685.

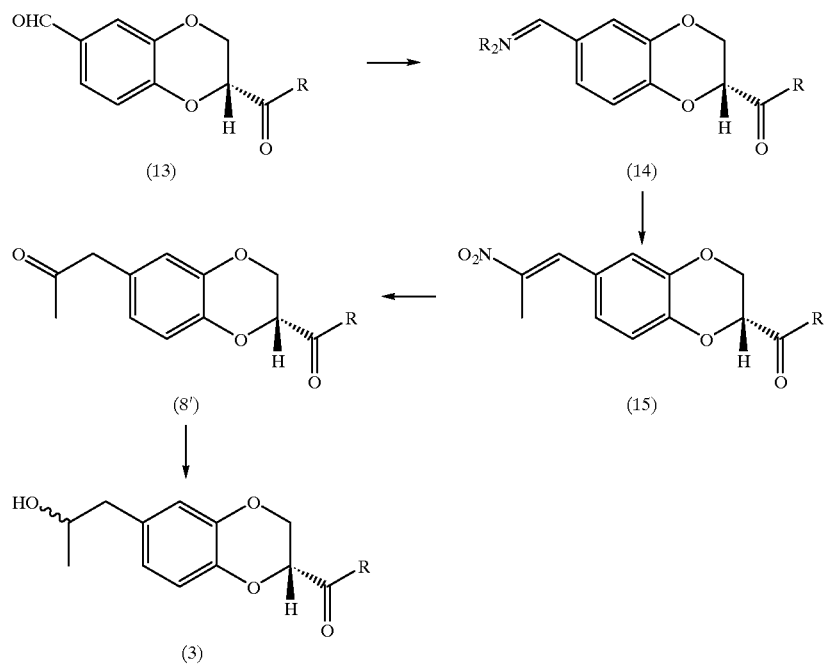

Scheme IV (R represents (R)-1-phenylethylamino or (S)-1-phenylethylamino.)

The present invention has been mentioned only about the preparation of 1,4-benzodioxin-2-carboxylic acid derivatives of formulae (1) and (2) starting from the compound of formula (13) wherein R is an optically active phenylethylamino group. These 1, 4-benzodioxin-2-carboxylic acid derivatives have the advantages that they are more chemically stable and are more difficult to be isomerized, as compared with conventional 1,4-benzodioxin-2-carboxylic acid derivatives starting from the compound of formula (13) wherein R is a $(C_1–C_4)$alkoxy group disclosed in WO 96/35685.

The reaction converting from a compound of formula (13) to a compound of formula (14) is carried out in the presence of primary amines and in the absence or presence of solvents. The reaction is carried out while dehydrating with Dean-Stark or using dehydrating agents such as anhydrous sodium carbonate, anhydrous potassium carbonate, anhydrous sodium sulfate, anhydrous magnesium sulfate, molecular sieves and the like. The primary amines used can include cyclohexylamine, methylamine, ethylamine and n-butylamine.

The solvents are not specifically limited unless giving any influence on the reaction, which can include ethers such as dimethyl ether, diethyl ether, diisopropyl ether, t-butyl methyl ether, tetrahydrofuran, dioxane and the like; alcohols such as methanol, ethanol, isopropanol, butanol, t-butyl alcohol and the like; aprotic polar solvents such as dimethylformamide, dimethylacetamide, dimethylsulfoxide and the like; hydrocarbons such as pentane, hexane, heptane, benzene, toluene, xylene and the like; halogenated hydrocarbons such as methylene chloride, chloroform, carbon tetrachloride, dichloroethane, trichloroethane and the like. The reaction can be carried out at a temperature ranging from 0° C. to reflux temperature of the solvent used. The reaction time usually ranges from 10 minutes to 10 hours, depending on the solvents used and a reaction temperature and so on. Preferably, the reaction can be performed for 1–5 hours, using hydrocarbons as a solvent under the reflux. More preferably, the reaction can be conducted for 1–3 hours, dehydrating in benzene under reflux.

The reaction converting from a compound of formula (14) to a compound of formula (15) is performed, using an acid in the absence or presence of solvents. The acids used can include inorganic acids such as hydrochloric acid, sulfuric acid and the like; organic acids such as acetic acid, propionic acid and the like; sulfonic acids such as methanesulfonic acid, toluenesulfonic acid, camphorsulfonic acid and the like. The solvents are not specifically limited unless giving any influence on the reaction, which can include ethers such as dimethyl ether, diethyl ether, diisopropyl ether, t-butyl methyl ether, tetrahydrofuran, dioxane and the like; alcohols such as methanol, ethanol, isopropanol, butanol, t-butyl alcohol and the like; aprotic polar solvents such as dimethylformamide, dimethylacetamide, dimethylsulfoxide and the like; hydrocarbons such as pentane, hexane, heptane, benzene, toluene, xylene and the like; halogenated hydrocarbons such as methylene chloride, chloroform, carbon tetrachloride, dichloroethane, trichloroethane and the like; organic acids such as acetic acid, propionic acid and the like. They can be used alone or in combination. The reaction can be carried out at a temperature ranging from 0° C. to reflux temperature of the solvent used. The reaction time varies depending on the solvents used and a reaction temperature, but usually ranges from 10 minutes to 10 hours. Preferably, the reaction can be carried out for 1–5 hours under the reflux, using organic acids such as acetic acid, propionic acid and the like as a solvent.

The reaction converting from a compound of formula (15) to a compound of formula (8') is carried out in the presence of a reducing agent. The reducing agents used can include metallic powders such as iron powder, zinc powder, copper powder and the like. The reaction is conducted in the presence of solvents. The solvents used are not specifically limited unless giving any influence on the reaction, which can include ethers such as tetrahydrofuran, dioxane and the like; alcohols such as methanol, ethanol, isopropanol, butanol, t-butyl alcohol and the like; aprotic polar solvents such as dimethylformamide, dimethylacetamide, dimethylsulfoxide and the like; organic acids such acetic acid, propionic acid and the like, and a mixed solvent of these. The reaction can be carried out at a temperature ranging from 0° C. to reflux temperature of the solvent used. The reaction time varies depending on solvents employed and a reaction temperature, but usually ranges from 10 minutes to 10 hours. Preferably, the reaction is carried out for 1–5 hours under the reflux, using a mixed solvent of water and alcohols such as methanol, ethanol and the like and organic acids such as acetic acid and the like.

The reaction converting from a compound of formula (8') to a compound of formula (3) is performed with a reducing agent. The reducing agents used can include metal hydrides such as lithium aluminum hydride ($LiAlH_4$), sodium borohydride ($NaBH_4$), lithium borohydride ($LiBH_4$), diborane ($B_2H_6$) and the like, and sodium borohydride or lithium borohydride is preferably used. The solvents which can be used depend on a reducing agent employed, which can include ethers such as diethyl ether, THF, dioxane and the like; alcohols such as methanol, ethanol, propanol and the like; and aromatic hydrocarbons such as benzene, toluene and the like.

The reaction temperature ranges from –20° C. to reflux temperature of solvents, preferably from 0° C. to room temperature. The reaction time depends on a reducing agent and solvents used, but ranges from one minute to 10 hours. Preferably, the reaction is carried out using sodium borohydride as a reducing agent in ethers or alcohols at a temperature of from 0° C. to room temperature for 30 minutes to 3 hours.

Optically active alcohols of formulae (1) and (2) according to the present invention are very useful as intermediates for the synthesis of 1,4-benzodioxin-2-carboxylic acid derivatives of formula (7'), which are useful as medicines, in high yield and with high optical purity.

According to the present invention, intermediates for the synthesis represented by formulae (1) and (2) can be also obtained in high yield and with high optical purity.

The present invention is illustrated in detail by the following examples and reference examples.

Analytical conditions for high performance liquid chromatography (HPLC) to determine optical purity and so on shown in examples are described below.

HPLC-1

Column: DEVELOSIL 60–3, 4.6 mm×500 mm (Nomura Chemical Co., LTD.)

Mobile phase: hexane/ethyl acetate/acetic acid=600/400/5

Flow rate: 1.0 ml/min

Detection: UV 280 nm

HPLC-2

Column: YMC CHIRAL NEA(R), 4.6 mm×300 mm (YMC Co., LTD.)

Mobile phase: 0.5 N sodium perchlorate-perchloric acid (pH 2.0)/acetonitrile=1/1

Flow rate: 1.0 ml/min
Detection: UV 280 nm
HPLC-3
Column: Nucleosil 50–5, 4.6 mm×250 mm
Mobile phase: ethyl acetate/hexane=1/1 (v/v)
Flow rate: 1.0 ml/min
Detection: UV 280 nm
Retention time: acetate 6.8 min, S alcohol 14.3 min, R alcohol 14.8 min The purities of optical isomers of formulae (1) and (2) are expressed in terms of values which are determined at the position of asymmetric carbon atoms in "hydroxypropyl" in the compounds. The purities of optical isomers of formulae (7) and (7') are expressed in terms of values which are determined at the position of asymmetric carbon atoms in "aminopropyl" in the compounds. The compound of formula (6) used is of optical purity 100%, and the starting material used in Reference Example 1 is of diastereomeric excess 97–99%.

EXAMPLE 1 a) 6-(2-(S)-hydroxypropyl)-2,3-dihydro-1,4-benzodioxin-(N-(1-(S)-phenylethyl))-2-(R)-carboxamide

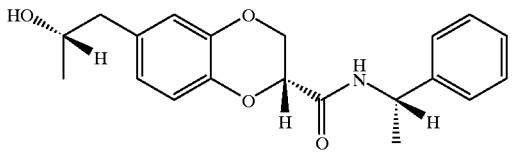

To a suspension of 6-(2-hydroxypropyl)-2,3-dihydro-1,4-benzodioxin-(N-( 1-(S)-phenylethyl))-2-(R)-carboxamide (1.1 g) in t-butyl methyl ether (200 ml) were added vinyl acetate (27 ml), 2,6-di-t-butyl-p-cresol (6.5 mg) and lipase PS (1.0 g, manufactured by Amano Pharmaceutical Co., Ltd.), and this mixture was stirred at 37° C. for 132 hours and at room temperature for 62 hours (The reaction was followed by HPLC 3, and stopped at the time of 50% acylation attained). After the reaction solution was filtered through Celite, the solvent was distilled off under reduced pressure. The residue was chromatographed over silica gel to give 6-(2-(R)-acetoxypropyl)-2,3-dihydro-1,4-benzodioxin-( N-(1-(S)-phenylethyl))-2-(R)-carboxamide (574 mg) as colorless crystals from the fraction of ethyl acetate/hexane (1/3) and 6-(2-(S)-hydroxypropyl)-2,3-dihydro-1,4-benzodioxin-( N-(1-(S)-phenylethyl))-2-(R)-carboxamide (510 mg, yield=46.4%) as colorless crystals from the fraction of ethyl acetate/hexane (1/1). The HPLC-1 analysis of the latter showed 95.1% purity for the optical isomer (S-alcohol isomer/R-alcohol isomer=95.1/4.9). 6-(2-(R)-acetoxypropyl)-2,3-dihydro-1,4-benzodioxin-(N-(1-(S)-phenylethyl))-2-(R)-carboxamide $^1$H-NMR (CDCl$_3$) δ: 1.20 (d, J=5.9Hz, 3H), 1.55 (d, J=6.8Hz, 3H), 2.00 (s, 3H), 2.65 (dd, J=6.3, 13.7Hz, 1H), 2.82 (dd, J=6.8, 14.2Hz, 1H), 4.12 (dd, J=7.3, 11.2Hz, 1H), 4.51 (dd, J=2.4, 11.2Hz, 1H), 4.69 (dd, J=2.4, 7.3Hz, 1H), 5.05 (sixt., J=6.3Hz, 1H), 5.18 (quint., J=7.3Hz, 1H), 6.71 (dd, J=2.0, 8.3Hz, 1H), 6.74 (d, J=2.0Hz, 1H), 6.78 (brd, J=8.3Hz, 1H), 6.87 (d, J=8.3Hz, 1H), 7.15–7.35 (m, 5H) 6-(2-(S)-hydroxypropyl)-2,3-dihydro-1,4-benzodioxin-(N-(1-(S)-phenylethyl))-2-(R)-carboxamide $^1$H-NMR (CDCl$_3$) δ: 1.22 (d, J=5.9Hz, 3H), 1.55 (d, J=6.8Hz, 3H), 1.62 (brs, 1H, D$_2$0 exchangeable), 2.59 (dd, J=7.8, 13.7Hz, 1H), 2.69 (dd, J=4.9, 13.7Hz, 1H), 3.96 (sixt., J=6.3Hz, 1H), 4.14 (dd, J=7.3, 11.7Hz, 1H), 4.51 (dd, J=2.9, 11.7Hz, 1H), 4.69 (dd, J=2.4, 7.3Hz, 1H), 5.18 (quint., J=7.3Hz, 1H), 6.77 (s, 1H), 6.79 (brs, 1H), 6.90 (d, J=8.3Hz, 1H), 7.15–7.27 (m, 5H)

b) 6-(2-(R)-hydroxypropyl)-2,3-dihydro-1,4-benzodioxin-(N-(1-(S)-phenylethyl))-2-(R)-carboxamide

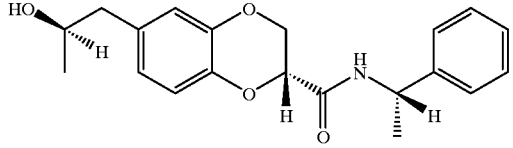

To a solution of 6-(2-(R)-acetoxypropyl)-2,3-dihydro-1,4-benzodioxin-( N-(1-(S)-phenylethyl))-2-(R)-carboxamide (574 mg) obtained in a) above in methanol (5 ml) was added potassium carbonate (6.2 mg), and the solution was stirred at room temperature for 12 hours. Potassium carbonate (14.5 mg) was further added, and the mixture was stirred for 14 hours. The solvent was distilled off under reduced pressure. The residue was dissolved in ethyl acetate, and washed with water. The resulting solution was dried over magnesium sulfate to give 6-(2-(R)-hydroxypropyl )-2,3-dihydro-1,4-benzodioxin-(N-(1-(S)-phenylethyl))-2-(R)-carboxamide (550 mg, yield=50%). The HPLC-1 analysis of the optical isomer showed 83.0% purity (S-alcohol isomer/R-alcohol isomer=17.0/83.0).

$^1$H-NMR (CDCl$_3$) δ: 1.22 (d, J=5.9Hz, 3H), 1.55 (d, J=6.8Hz, 3H), 1.62 (brs, 1H, D$_2$O exchangeable), 2.59 (dd, J=7.8, 13.7Hz, 1H), 2.69 (dd, J=4.9, 13.7Hz, 1H), 3.96 (sixt., J=6.3Hz, 1H), 4.14 (dd, J=7.3, 11.7Hz, 1H), 4.51 (dd, J=2.9, 11.7Hz, 1H), 4.69 (dd, J=2.4, 7.3Hz, 1H), 5.18 (quint., J=7.3Hz, 1H), 6.77 (s, 1H), 6.79 (brs, 1H), 6.90 (d, J=8.3Hz, 1H), 7.15–7.27 (m, 5H)

EXAMPLE 2 a) To a solution of 6-(2-hydroxypropyl)-2,3-dihydro-1,4-benzodioxin-( N-(1-(S)-phenylethyl))-2-(R)-carboxamide (1.0 g) in tetrahydrofuran (20 ml) were added vinyl acetate (13.5 ml) and 2,6-di-t-butyl-p-cresol (6.4 mg). This solution was stirred at 37° C. on a water bath, lipase AK (500 mg, manufactured by Amano Pharmaceutical Co., Ltd.) was added thereto, and the mixture was stirred at 37° C. on a water bath for 51 hours. The reaction solution was filtered through Celite, and then concentrated under reduced pressure. The residue was chromatographed over silica gel to give 6-(2-(R)-acetoxypropyl)-2,3-dihydro-1,4-benzodioxin-( N-(1-(S)-phenylethyl))-2-(R)-carboxamide (510 mg, yield=46%) from the fraction of ethyl acetate/hexane (2/3) and 6-(2-(S)-hydroxypropyl)-2,3-dihydro-1,4-benzodioxin-( N-(1-(S)-phenylethyl))-2-(R)-carboxamide (440 mg, yield=44%) from the fraction of ethyl acetate/hexane (3/2). The HPLC-1 analysis of the optical isomer showed 97.9% purity (S-alcohol isomer/R-alcohol isomer=97.9/2.1).

b) To a solution of 6-(2-(R)-acetoxypropyl)-2,3 -dihydro-1,4-benzodioxin-(N-(1-(S)-phenylethyl))-2-(R)-carboxamide (510 mg) obtained in a) above in methanol (15 ml) was added potassium carbonate (40 mg), and the solution was stirred at room temperature for 9 hours. The reaction solution was concentrated under reduced pressure, and the residue was chromatographed over silica gel to give 6-(2-(R )-hydroxypropyl)-2,3-dihydro-1,4-benzodioxin-(N-(1-(S)-phenylethyl))-2-(R)-carboxamide (430 mg, yield=43%) from the fraction of ethyl acetate/hexane (3/2). The HPLC-1 analysis of the optical isomer showed 96.9% purity (S-alcohol isomer/R-alcohol isomer=3.1/96.9).

EXAMPLE 3

6-(2-(R)-Hydroxypropyl)-2,3-dihydro-1,4-benzodioxin-( N-(1-(S)-phenylethyl))-2-(R)-carboxamide (yield=21%, the purity of the optical isomer=70.0% by HPLC-1 analysis(S-alcohol isomer/R-alcohol isomer=30/70)) was prepared in a similar manner as in Example 1a), except for using t-butyl methyl ether as a solvent and DLIP-300 (manufactured by Toyobo) as lipase. 6-(2-(S)-hydroxypropyl )-2 ,3-dihydro-1,4-benzodioxin-(N-(1-(S)-phenylethyl))-2-(R)-carboxamide (yield=79%, the purity of the optical isomer= 54.2% by HPLC-1 analysis (S-alcohol isomer/R-alcohol isomer=54.2/45.8)) was also obtained in a similar way as in Example 1b). Yield was calculated by HPLC-3 analysis.

EXAMPLE 4

6-(2-(S)-Hydroxypropyl)-2,3-dihydro-1,4-benzodioxin-( N-(1-(S)-phenylethyl))-2-(R)-carboxamide (yield=52%, the purity of the optical isomer=96.4% by HPLC-1 analysis (S-alcohol isomer/R-alcohol isomer=96.4/3.6)) was obtained in a similar way as in Example 1a), except for using toluene as a solvent and lipase AK (manufactured by Amano Pharmaceutical Co., Ltd.) as lipase. 6-(2-(R)-Hydroxypropyl )-2,3-dihydro-1,4-benzodioxin-(N-(1-(S)-phenylethyl))-2-(R)-carboxamide (yield=48%, the purity of the optical isomer=91.1% by HPLC-1 analysis (S-alcohol isomer/R-alcohol isomer=8.9/91.1)) was also obtained in a similar way as in Example 1b). Yield was calculated by HPLC-3 analysis.

EXAMPLE 5

6-(2-(S)-Hydroxypropyl)-2,3-dihydro-1,4-benzodioxin-( N-(1-(S)-phenylethyl))-2-(R)-carboxamide (yield=50%, the purity of the optical isomer=94.1% by HPLC-1 analysis (S-alcohol isomer/R-alcohol isomer=94.1/5.9)) was obtained in a similar way as in Example 1a), except for using methyl ethyl ketone as a solvent and lipase AK (manufactured by Amano Pharmaceutical Co., Ltd.) as lipase. 6-(2-(R)-Hydroxypropyl)-2,3-dihydro-1,4-benzodioxin-(N-(1-( S)-phenylethyl))-2-(R)-carboxamide (yield=50%, the purity of the optical isomer=97.6% by HPLC-1 analysis (S-alcohol isomer/R-alcohol isomer=2.4/97.6)) was also obtained in a similar way as in Example 1b). Yield was calculated by HPLC-3 analysis.

EXAMPLE 6

6-(2-(S)-Hydroxypropyl)-2,3-dihydro-1,4-benzodioxin-( N-(1-(S)-phenylethyl))-2-(R)-carboxamide (yield=51%, the purity of the optical isomer=98.5% by HPLC-1 analysis (S-alcohol isomer/R-alcohol isomer=98.5/1.5)) was obtained in a similar way as in Example 1a), except for using acetonitrile as a solvent and lipase AK (manufactured by Amano Pharmaceutical Co., Ltd.) as lipase. 6-(2-(R)-Hydroxypropyl )-2,3-dihydro-1,4-benzodioxin-(N-(1-(S)-phenylethyl))-2-(R)-carboxamide (yield=49%, the purity of the optical isomer=95.0% by HPLC-1 analysis (S-alcohol isomer/R-alcohol isomer=5.0/95.0)) was also obtained in a similar way as in Example 1b). Yield was calculated by HPLC-3 analysis.

EXAMPLE 7

6-(2-(S)-(p-Toluenesulfonyloxy)propyl)-2,3-dihydro-1,4-benzodioxin-( N-(1-(S)-phenylethyl))-2-(R)-carboxamide

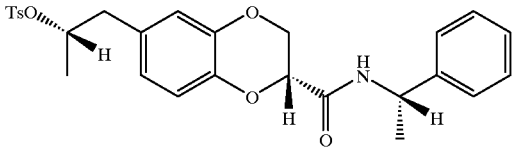

To a solution of 6-(2-(S)-hydroxypropyl)-2,3-dihydro-1, 4-benzodioxin-( N-(1-(S)-phenylethyl))-2-(R)-carboxamide (1.6 g) in methylene chloride (15 ml) were added 4-dimethylaminopyridine (860 mg) and p-toluenesulfonyl chloride (1.34 g) at room temperature, and the mixture was stirred for 24 hours. To the reaction solution was added chloroform, and this solution was washed in turn with dilute hydrochloric acid, aqueous sodium hydrogencarbonate and saturated brine, and dried over magnesium sulfate. The solvent was distilled off under reduced pressure. The residue was chromatographed over silica gel to give 6-(2-( S)-(p-toluenesulfonyloxy)propyl)-2,3-dihydro-1,4-benzodioxin-( N-(1-(S)-phenylethyl))-2-(R)-carboxamide (2.18 g, yield= 94%) as a colorless oil from the fraction of ethyl acetate/hexane (1/2).

$^1$H-NMR (CDCl$_3$) δ: 1.24 (d, J=6.3Hz, 3H), 1.55 (d, J=6.8Hz, 3H), 1.60 (d, J=11.4Hz, 1H), 2.41 (s, 3H), 2.68 (dd, J=6.8, 13.7Hz, 1H), 2.82 (dd, J=6.3, 14.2Hz, 1H), 4.05–4.15 (m, 1H), 4.51 (dd, J=2.9, 11.7Hz, 1H), 4.65–4.72 (m, 1H), 5.27 (quint., J=7.8Hz, 1H), 6.40–6.65 (m, 2H), 6.75–6.85 (m, 2H), 7.15–7.33 (m, 6H), 7.68 (d, J=8.3Hz, 2H)

EXAMPLE 8

6-(2-(R)-(p-Toluenesulfonyloxy)propyl)-2,3-dihydro-1, 4-benzodioxin-( N-(1-(S)-phenylethyl))-2-(R)-carboxamide

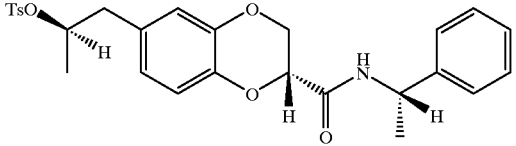

6-(2-(R)-(p-Toluenesulfonyloxy)propyl)-2,3-dihydro-1, 4-benzodioxin-( N-(1-(S)-phenylethyl))-2-(R)-carboxamide was obtained in 64% yield in a similar way as in Example 7 from 6-(2-(R)-hydroxypropyl)-2,3-dihydro-1,4-benzodioxin-( N-(1-(S)-phenylethyl))-2-(R)-carboxamide.

$^1$H-NMR (CDCl$_3$) δ: 1.24 (d, J=6.3Hz, 3H), 1.55 (d, J=6.8Hz, 3H), 1.60 (d, J=11.4Hz, 1H), 2.41 (s, 3H), 2.68 (dd, J=6.8, 13.7Hz, 1H), 2.82 (dd, J=6.3, 14.2Hz, 1H), 4.05–4.15 (m, 1H), 4.51 (dd, J=2.9, 11.7Hz, 1H), 4.65–4.72 (m, 1H), 5.27 (quint., J=7.8Hz, 1H), 6.40–6.65 (m, 2H), 6.75–6.85 (m, 2H), 7.15–7.33 (m, 6H), 7.68 (d, J=8.3Hz, 2H)

EXAMPLE 9

To a solution of 6-(2-(R)-hydroxypropyl)-2,3-dihydro-1, 4-benzodioxin-( N-(1-(S)-phenylethyl))-2-(R)-carboxamide (1.0 g) in methylene chloride (12 ml) were added triphenylphosphine (1.15 g) and carbon tetrabromide (1.46 g).

The solution was stirred at room temperature for 3 hours and then washed in turn with a saturated aqueous solution of sodium hydrogencarbonate and saturated brine, dried over magnesium sulfate, and concentrated under reduced pressure. The residue was chromatographed over silica gel to give 6-(2-(S)-bromopropy1-2,3-dihydro-1,4-benzodioxin-(N-(1-(S)-phenylethyl))-2-(R)-carboxamide (940 mg, yield= 79%) from the fraction of ethyl acetate/hexane (1/2).

$^1$H-NMR (CDCl$_3$) δ: 1.55 (d, 3H, J=8.4Hz), 1.67 (d, 3H, J=6.8Hz), 2.97 (dd, 1H, J=7.2Hz, 14.4Hz), 3.11 (dd, 1H, J=7.2Hz, 14.4Hz), 4.09–4.28 (m, 2H), 4.51 (dd, 1H, J=2.8Hz, 11.6Hz), 4.70 (dd, 1H, J=2.8Hz, 7.6Hz), 5.18 (quint. 1H, 7.2Hz), 6.68–6.80 (m, 3H), 6.85–6.92 (m, 1H), 7.15–7.33 (m, 5H)

EXAMPLE 10

To a solution of 6-(2-(R)-hydroxypropyl)-2,3-dihydro-1,4-benzodioxin-( N-(1-(S)-phenylethyl))-2-(R)-carboxamide (1.0 g) in carbon tetrachloride (15 ml) was added triphenylphosphine (1.23 g). This solution was stirred under reflux for 6 hours, and ethyl acetate was added thereto. The mixture was filtered through Celite, and then concentrated under reduced pressure. The residue was chromatographed over silica gel to give 6-(2-(S )-chioropropyl)-2,3-dihydro-1,4-benzodioxin-(N-(1-(S)-phenylethyl) )-2-(R)-carboxamide (780 mg, yield=74%) from the fraction of ethyl acetate/hexane (1/2).

$^1$H-NMR (CDCl$_3$) δ: 1.48 (d, 3H, J=6.8Hz), 1.55 (d, 3H, J=6.8Hz), 2.87 (dd, 1H, J=6.8Hz, 14.4Hz), 2.97 (dd, 1H, J=6.8Hz, 14.4Hz), 4.08–4.21 (m, 2H), 4.51 (dd, 1H, J=2.4Hz, 11.2Hz), 4.70 (dd, 1H, J=2.4Hz, 7.2Hz), 5.18 (quint, 1H, J=7.2Hz), 6.70–6.82 (m, 3H), 6.85–6.93 (m, 1H), 7.15–7.32 (m, 5H)

EXAMPLE 11

To a solution of 6-(2-(R)-hydroxypropyl)-2,3-dihydro-1,4-benzodioxin-( N-(1-(S)-phenylethyl))-2-(R)-carboxamide (200 mg) in tetrahydrofuran (6 ml) and acetonitrile (2 ml) were added in turn triphenylphosphine (185 mg), imidazole (48 mg) and iodine (179 mg) at room temperature. The mixture was stirred for 5 hours, and triphenylphosphine (185 mg), imidazole (48 mg) and iodine (90 mg) were further added thereto. After stirring for ten minutes, ethyl acetate was added to the reaction solution. This solution was washed in turn with a saturated aqueous solution of sodium hydrogencarbonate, a 10% aqueous solution of sodium thiosulfate and saturated brine, and then dried over sodium sulfate. The solvent was distilled off under reduced pressure. The residue was chromatographed over silica gel to give 6-(2-(S)-iodopropyl)-2,3-dihydro-1,4-benzodioxin-( N-(1-(S)-phenylethyl))-2-(R)-carboxamide (230 mg, yield=87%) from the fraction of ethyl acetate/hexane (1/3 –1/2).

$^1$H-NMR (CDCl$_3$) δ: 1.55 (d, J=6.8Hz, 3H), 1.88 (d, J=6.8Hz, 3H), 2.96 (dd, J=7.3, 14.2Hz, 1H), 3.17 (dd, J=7.3, 14.2Hz, 1H), 4.15 (dd, J=7.3, 12.2Hz, 1H), 4.27 (dd, J=7.3, 14.2Hz, 1H), 4.51 (dd, J=2.9, 11.2Hz, 1H), 4.70 (dd, J=2.9, 7.3Hz, 1H), 5.18 (quint., J=7.3Hz, 1H), 6.70 (dd, J=2.0, 8.3Hz, 1H), 6.73 (d, J=2.0Hz, 1H), 6.77 (brd, J=8.0Hz, 1H), 6.89 (d, J=8.3Hz, 1H), 7.15–7.32 (m, 5H)

EXAMPLE 12

6-(2-(R)-((2-(R)-(3-Chlorophenyl)-2-hydroxyethyl)amino)-propyl )-2,3-dihydro-1,4-benzodioxin-(N-(1-(s)-phenylethyl))-2-(R)-carboxamide

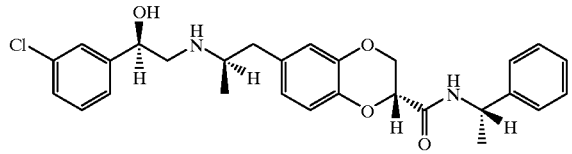

To 6-(2-(S)-chloropropyl)-2,3-dihydro-1,4–20 benzodioxin-( N-(1-(s)-phenylethyl))-2-(R)-carboxamide (360 mg) was added (R)-2-amino-1-(3-chlorophenyl)-ethanol (686 mg), the mixture was stirred at 130° C. for 14 hours, and then ethyl acetate was added thereto. The reaction solution was washed in turn with a saturated aqueous solution of sodium hydrogencarbonate and saturated brine, then dried over sodium sulfate and concentrated under reduced pressure. The residue was chromatographed over silica gel to give 6-(2-(R)-((2-(R)-(3-chlorophenyl)-2-hydroxyethyl)amino)-propyl )-2,3-dihydro-1,4-benzodioxin-(N-(1-(S)-phenylethyl))-2-(R)-carboxamide (150 mg, yield=30%) from the fraction of methanol/ethyl acetate/aqueous ammonia (10/90/1). The HPLC-2 analysis of the optical isomer showed 91.5% purity (R/S=91.5/8.5, the purity of the material optical isomer used=97.5%).

$^1$H-NMR (CDCl$_3$) δ: 1.08 (d, J=6.3Hz, 3H), 1.55 (d, J=7.3Hz, 3H), 2.50–2.95 (m, 7H, 2H:D$_2$O exchangeable), 4.12 (dd, J=7.3, 11.2Hz, 1H), 4.52 (dd, J=2.4, 11.2Hz, 1H), 4.58 (dd, J=3.4, 8.8Hz, 1H), 4.69 (dd, J=2.4, 7.3Hz, 1H), 5.18 (quint., J=7.3Hz, 1H), 6.68 (dd, J=2.0, 8.3Hz, 1H), 6.72 (d, J=1.5Hz, 1H), 6.79 (brd, J=8.3Hz, 1H), 6.89 (d, J=8.3Hz, 1H), 7.15–7.35 (m, 9H)

EXAMPLE 13

To 6-(2-(S)-iodopropyl)-2,3-dihydro-1,4-benzodioxin-( N-(1-(S)-phenylethyl))-2-(R)-carboxamide (450 mg) was added (R)-2-amino-1-(3-chlorophenyl)-ethanol (686 mg), the mixture was stirred at 100° C. for one hour, and then ethyl acetate was added thereto. After this reaction solution was washed in turn with a saturated aqueous solution of sodium hydrogencarbonate and saturated brine, dried over sodium sulfate and then concentrated under reduced pressure. The residue was chromatographed over silica gel to give 6-(2-(R)-((2-(R)-(3-chlorophenyl)-2-hydroxyethyl)amino)propyl)-2,3-dihydro-1,4-benzodioxin-(N-(1-(S)-phenylethyl))-2-(R)-carboxamide (180 mg, yield=36%) from the fraction of methanol/ethyl acetate/aqueous ammonia (10/90/1). The HPLC-2 analysis of the optical isomer showed 73% purity (R/S=73/27, the purity of the material optical isomer used=97.5%).

EXAMPLE 14

To 6-(2-(S)-bromopropyl)-2,3-dihydro-1,4-benzodioxin-( N-(1-(S)-phenylethyl))-2-(R)-carboxamide (280 mg) was added (R)-2-amino-1-(3-chlorophenyl)-ethanol (177 mg), the mixture was stirred at 100° C. for one hour, and then chloroform was added thereto. This reaction solution was washed in turn with a saturated aqueous solution of sodium hydrogencarbonate and saturated brine, dried over sodium sulfate, and then concentrated under reduced pressure. The residue was chromatographed over silica gel to give 6-(2-(R)-((2-(R)-(3-chlorophenyl)-2-hydroxyethyl)amino)-propyl )-2,3-dihydro-1,4-benzodioxin-(N-(1-(S)-phenylethyl))-2-(R)-carboxamide (160 mg, yield=32%) from the fraction of methanol/ethyl acetate/aqueous ammonia (10/90/1). The HPLC-2 analysis of the optical isomer showed 75% purity (R/S=75/25, the purity of the material optical isomer used=97.5%).

EXAMPLE 15

To 6-(2-(S)-(p-toluenesulfonyloxy)propyl)-2,3-dihydro-1,4-benzodioxin-( N-(1-(S)-phenylethyl))-2-(R)-carboxamide (48.3 g) was added (R)-2-amino-1-(3-chlorophenyl)-ethanol (66.9 g) dissolved in a small amount of methylene chloride. The mixture was concentrated under reduced pressure. After removing methylene chloride, the solution was stirred at 70–85° C. for 4 hours. Ethyl acetate (1.0 L) was added to the reaction solution, and the solution was twice washed with a saturated aqueous solution of sodium hydrogencarbonate, dried over sodium sulfate, and concentrated under reduced pressure. The residue was chromatographed over silica gel to give 6-(2-(R)-((2-(R)-(3-chlorophenyl )-2-hydroxyethyl)amino)propyl)-2,3-dihydro-1,4-benzodioxin-( N-(1-(S)-phenylethyl))-2-(R)-carboxamide (34.5 g, yield=71%) from the fraction of methanol/ethyl acetate/aqueous ammonia (10/90/1). The HPLC-2 analysis of the optical isomer showed 92.2% purity (R/S=92.2/7.8, the purity of the material optical isomer used=97.5%).

EXAMPLE 16

To a solution of 6-(2-(S)-iodopropyl)-2,3-dihydro-1,4-benzodioxin-( N-(1-(S)-phenylethyl))-2-(R)-carboxamide (450 mg) in toluene (6 ml) were added (R)-2-amino-1-(3-chlorophenyl)-ethanol (343 mg) and sodium hydrogencarbonate (252 mg), and the mixture was stirred under reflux-heating for 61 hours. To the reaction solution was added water, and the mixture was extracted with ethyl acetate. The organic layer was dried over sodium sulfate and then concentrated under reduced pressure. The residue was chromatographed over silica gel to give 6-(2-(R)-((2-(R)-(3-chlorophenyl)-2-hydroxyethyl) amino)propyl)-2,3-dihydro-1,4-benzodioxin-( N-(1-(S)-phenylethyl))-2-(R)-carboxamide (210 mg, yield=42%) from the fraction of methanol/ethyl acetate/aqueous ammonia (10/90/1). The HPLC-2 analysis of the optical isomer showed 67.5% purity (R/S=67.5/32.5, the purity of the material optical isomer used=97.5%).

EXAMPLE 17

6-(2-(R)-((2-(R)-(3-chlorophenyl)-2-hydroxyethyl) amino)propyl)-2,3-dihydro-1,4-benzodioxin-( N-(1-(S)-phenylethyl))-2-(R)-carboxamide was obtained in 34% yield in a similar way as in Example 16, except for using 6-(2-(S)-bromopropyl)-2,3-dihydro-1,4-benzodioxin-(N-(1-(S)-phenylethyl) )-2-(R)-carboxamide as a starting material and potassium carbonate as a base. The HPLC-2 analysis of the optical isomer showed 96.5% purity (R/S=96.5/3.5, the purity of the material optical isomer used=97.5%).

EXAMPLE 18

Ethyl 6-(2-(R)-( (2-(R)-(3-chlorophenyl)-2-hydroxyethyl)-amino) propyl)-2,3-dihydro-1,4-benzodioxin-2-(R)-carboxylate

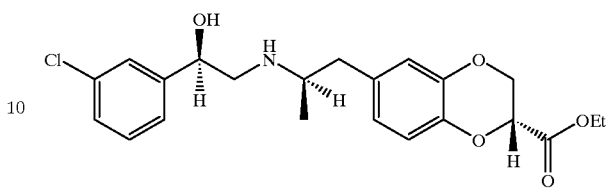

To a solution of 6-(2-(R)-((2-(R)-( 3-chlorophenyl)-2-hydroxyethyl)amino)propyl)-2,3-dihydro-1,4-benzodioxin-( N-(1-(S)-phenylethyl))-2-(R)-carboxamide (1.0 g) in acetic acid (12 ml) and water (12 ml) was added concentrated sulfuric acid (1.5 ml), and the mixture was stirred at 100° C. for 42 hours. After the solution was concentrated under reduced pressure, the residue was dissolved in ethanol (20 ml) and the solution was again concentrated under reduced pressure. This procedure was carried out three times, the resulting solution was partitioned between ethyl acetate and a saturated aqueous solution of sodium hydrogencarbonate, and the ethyl acetate layer was washed with saturated brine, dried over sodium sulfate, and concentrated under reduced pressure. The residue was chromatographed over silica gel to give ethyl 6-(2-(R)-((2-(R)-(3-chlorophenyl)-2-hydroxyethyl)amino )-propyl)-2,3-dihydro-1,4-benzodioxin-2-(R)-carboxylate (690 mg, yield=82%) from the fraction of methanol/ethyl acetate/aqueous ammonia (10/90/1). The HPLC-2 analysis of the optical isomer showed 90.5% purity (R/s=90.5/9.5, the purity of the material optical isomer used=90.5%).

$^1$H-NMR (CDCl$_3$) δ: 1.06 (d, J=6.3Hz, 3H), 1.29 (t, J=7.3Hz, 3H), 2.50–2.65 (m, 3H), 2.84–2.91 (m, 2H), 4.22–4.32 (m, 2H), 4.37 (d, J=3.4Hz, 2H), 4.52 (dd, J=3.4, 8.8Hz, 1H), 4.80 (t, J=3.9Hz, 1H), 6.64–6.73 (m, 2H), 6.93 (d, J=8.3Hz, 1H), 7.19–7.30 (m, 3H), 7.35 (s, 1H)

EXAMPLE 19

6-(2-(R)-((2-(R)-(3-chlorophenyl)-2-hydroxyethyl) amino)-propyl )-2,3-dihydro-1,4-benzodioxin-2-(R)-carboxylic acid

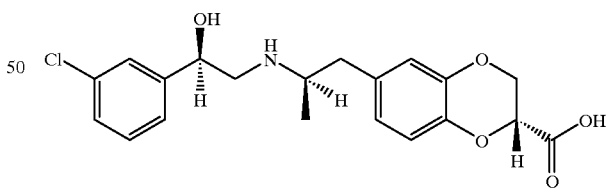

To a solution of ethyl 6-(2-(R)-((2-(R)-(3-chlorophenyl )-2-hydroxyethyl)amino)propyl)-2,3-dihydro-1,4-benzodioxin-2-(R)-carboxylate (650 mg) in ethanol (2 ml) were added water (20 ml) and concentrated hydrochloric acid (0.32 ml). This solution was stirred under reflux-heating for 5 hours while removing ethanol with Dean-Stark apparatus. After the solution was concentrated under reduced pressure, acetonitrile/water (1/1) (11 ml) was added to the residue, which was then dissolved under heating. The solution was neutralized with a 5% aqueous solution of sodium hydrogencarbonate. Acetonitrile (20 ml) was added, and the crystals precipitated were dissolved under heating. The resulting solution was filtered under heating and then cooled, and the resulting crystals were filtered to give 6-(2-(R)-((2-(R)-(3-chlorophenyl)-2-hydroxyethyl)amino)-propyl)-2,3-dihydro-1,4-benzodioxin-2-(R)-carboxylic acid (412 mg). The HPLC-2 analysis of the optical isomer showed 96.5% purity (R/S=96.5/3.5, the purity of the material optical isomer used=90.5%).

White crystals, m.p. 243–244° C. (dec.)

$^1$H-NMR (DMSO-$d_6$) δ: 0.81 (d, J-6.3Hz, 3H), 1.88 (t, J=12. 2Hz, 1H), 2.26 (d, J=11.7Hz, 1H), 2.80 (dt, J=11.2Hz, 1H), 3.00–3.17 (m, 2H), 4.10 (d, J=8.8Hz, 1H), 4.52 (brd, J=10.2Hz, 1H), 4.67 (s, 1H), 5.19 (brd, J=8.8Hz, 1H), 6.26 (brd, J=8.3Hz, 1H), 6.39 (brs, 1H), 6.74 (d, J=8.3Hz, 1H), 7.30–7.42 (m, 3H), 7.47 (brs, 1H)

$^{13}$C-NMR (DMSO-$d_6$) δ: 13.8, 37.6, 51.5, 55.0, 66.1, 66.8, 72.8, 116.7, 117.4, 121.6, 124.6, 125.7, 127.3, 129.0, 130.2, 133.1, 142.1, 142.9, 144.7, 172.9

EXAMPLE 20

To a solution of 6-(2-(R)-((2-(R)-(3-chlorophenyl )-2-hydroxyethyl)amino)propyl)-2,3-dihydro-1,4-benzodioxin-( N-(1-(S)-phenylethyl))-2-(R)-carboxamide (21 g) in acetic acid (100 ml) and water (100 ml) was added concentrated sulfuric acid (10 ml). This solution was stirred at external temperature of 120° C. for 58 hours. After the solution was cooled to room temperature, the pH was adjusted to about 3 with an aqueous solution of sodium acetate. The solution was extracted with chloroform, and concentrated under reduced pressure. To the residue was added acetonitrile/water (1/1) (210 ml) and the residue was dissolved under heating. The solution was neutralized with a saturated aqueous solution of sodium hydrogencarbonate, and about a half amount of the reaction solution was concentrated under ordinary pressure. The insolubles precipitated were dissolved under heating with ethanol (300 ml) and water (100 ml), and then the solution was cooled on an ice bath. The resulting crystals were filtered off to give 6-(2-(R)-((2-(R)-(3-chlorophenyl)-2-hydroxyethyl)-amino) propyl)-2,3-dihydro-1,4-benzodioxin-2-(R)-carboxylic acid (7.04 g). The HPLC-2 analysis of the optical isomer showed 97.4% purity (R/S=97.4/2.6, the purity of the material optical isomer used=84.3%).

EXAMPLE 21

6-(2-(R)-Hydroxypropyl)-2,3-dihydro-1,4-benzodioxin-(N-(1-(S)-phenylethyl))-2-(R)-carboxamide

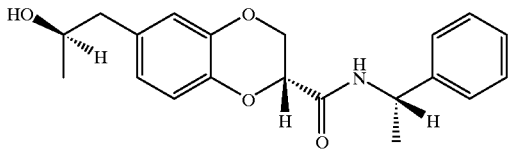

To a solution of 6-(2-(S)-hydroxypropyl)-2,3-dihydro-1,4-benzodioxin-( N-(1-(S)-phenylethyl))-2-(R)-carboxamide (0.5 g) in tetrahydrofuran (5 ml) were added in turn under ice-cooling triethylamine (0.31 ml) and methanesulfonyl chloride (0.14 ml). This solution was stirred under ice-cooling for 15 minutes. After adding ethyl acetate, the mixture was washed in turn with dilute hydrochloric acid, an aqueous solution of sodium hydrogencarbonate and saturated brine, dried over magnesium sulfate, and the solvent was distilled off under reduced pressure. To a solution of the residue in dimethylformamide (15 ml) was added cesium propionate (0.9 g), and the mixture was stirred at 50° C. for 62 hours. Ethyl acetate was added, and the mixture was washed in turn with water, dilute hydrochloric acid, an aqueous solution of sodium hydrogencarbonate and saturated brine, dried over magnesium sulfate, and the solvent was distilled off under reduced pressure. Potassium carbonate (14 mg) was added to a solution of the residue in methanol (10 ml), the mixture was stirred at room temperature for 46 hours, and the solvent was then distilled off under reduced pressure. The residue was chromatographed over silica gel to give 6-(2-(R)-hydroxypropyl )-2,3-dihydro-1,4-benzodioxin-(N-(1-(S)-phenylethyl))-2-(R)-carboxamide (0.28 g, yield=56%) from the fraction of ethyl acetate/hexane (2/1). The HPLC-1 analysis of the optical isomer showed 95.5% purity (R/S=95.5/4.5, the purity of the material optical isomer used=96%).

EXAMPLE 22

To a solution of 6-(2-(S)-hydroxypropyl)-2,3-dihydro-1, 4-benzodioxin-( N-(1-(s)-phenylethyl))-2-(R)-carboxamide (0.5 g) in methylene chloride (8 ml) were added 4-dimethylaminopyridine (450 mg) and p-toluenesulfonyl chloride (560 mg) at room temperature, and the mixture was stirred for 24 hours. To the reaction solution was added chloroform, the solution was washed in turn with dilute hydrochloric acid, an aqueous solution of sodium hydrogencarbonate and saturated brine, dried over magnesium sulfate, and the solvent was distilled off under reduced pressure. Dimethylformamide (13 ml) was added to the residue, and the mixture was stirred at 75° C. for 24 hours, and then the solvent was distilled off under reduced pressure. Potassium carbonate (18 mg) was added to a solution of the residue in methanol (10 ml), the mixture was stirred at room temperature for 21 hours, and the solvent was distilled off under reduced pressure. The residue was chromatographed over silica gel to give 6-(2-(R )-hydroxypropyl)-2,3-dihydro-1,4-benzodioxin-(N-(1-(S)-phenylethyl))-2-(R)-carboxamide (0.36 g, yield=72%) from the fraction of ethyl acetate/hexane (⅔). The HPLC-1 analysis of the optical isomer showed 84% purity (R/S=84/16, the purity of the material optical isomer used=96%).

EXAMPLE 23

6-(2-(S)-Hydroxypropyl)-2,3-dihydro-1,4-benzodioxin-(N-(1-(S )-phenylethyl))-2-(R)-carboxamide

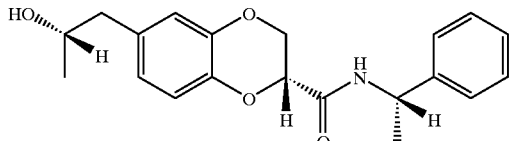

To a solution of 6-(2-(R)-hydroxypropyl)-2,3-dihydro-1, 4-benzodioxin-( N-(1-(S)-phenylethyl))-2-(R)-carboxamide (1.0 g) in methylene chloride (16 ml) were added 4-dimethylaminopyridine (900 mg) and p-toluenesulfonyl chloride (1.12 g) at room temperature, and the solution was stirred for 24 hours. To the reaction solution was added chloroform, the mixture was washed in turn with dilute hydrochloric acid, an aqueous solution of sodium hydrogencarbonate and saturated brine, dried over magnesium sulfate, and the solvent was distilled off under reduced pressure. To a solution of the residue in dimethylformamide (10 ml) was added sodium acetate (250 mg), and the mixture was stirred at 60° C. for 64 hours. Ethyl acetate was added and the mixture was washed in turn with water, dilute hydrochloric acid, an aqueous solution of sodium hydrogencarbonate and saturated brine, dried over magnesium sulfate, and the solvent was distilled off under reduced pressure. To a solution of the residue in methanol (20 ml) was added potassium carbonate (42 mg), and the solution was stirred at room temperature for 24 hours. The solvent was distilled off under reduced pressure to give 6-(2-(S )-hydroxypropyl)-2,3-dihydro-1,4-benzodioxin-(N-(1-(S)-phenylethyl) )-2-(R)-carboxamide (yield=61%, the purity of the optical isomer= 83.5% by HPLC-1 analysis (S/R=83.5/16.5, the purity of the material optical isomer used=96% )).
Yield was calculated by HPLC-3 analysis.

EXAMPLE 24

To a solution of 6-(2-(R)-hydroxypropyl)-2,3-dihydro-1,4-benzodioxin-( N-(1-(S)-phenylethyl))-2-(R)-carboxamide (0.5 g) in methylene chloride (8 ml) were added 4-dimethylaminopyridine (450 mg) and p-toluenesulfonyl chloride (560 mg) at room temperature, and the solution was stirred for 24 hours. To the reaction solution was added chloroform, the mixture was washed in turn with dilute hydrochloric acid, an aqueous solution of sodium hydrogencarbonate and saturated brine, dried over magnesium sulfate, and the solvent was distilled off under reduced pressure. To a solution of the residue in dimethylsulfoxide (5 ml) was added ammonium formate (280 mg), and the mixture was stirred at 50° C. for 24 hours. To the solution was added ethyl acetate, and the mixture was washed in turn with dilute hydrochloric acid, an aqueous solution of sodium hydrogencarbonate and saturated brine, dried over magnesium sulfate, and the solvent was distilled off under reduced pressure. To a solution of the residue in methanol (20 ml) was added p-toluenesulfonic acid monohydrate (20 mg), the solution was stirred at 60° C. for one hour, and the solvent was distilled off under reduced pressure. To the solution was added ethyl acetate, the mixture was washed in turn with water, dilute hydrochloric acid, an aqueous solution of sodium hydrogencarbonate and saturated brine, dried over magnesium sulfate. The solvent was distilled off under reduced pressure to give 6-(2-(S)-hydroxypropyl)-2,3-dihydro-1,4-benzodioxin-( N-(1-(S)-phenylethyl))-2-(R)-carboxamide (yield=71%, the purity of the optical isomer= 95% by HPLC-1 analysis (S/R=95/5, the purity of the material optical isomer used=96%)). Yield was calculated by HPLC-3 analysis.

EXAMPLE 25

To a solution of 6-(2-(R)-hydroxypropyl)-2,3-dihydro-1,4-benzodioxin-( N-(1-(S)-phenylethyl))-2-(R)-carboxamide (7.0 g) in tetrahydrofuran (70 ml) were added in turn under ice-cooling triethylamine (4.3 ml) and methanesulfonyl chloride (1.9 ml). This solution was stirred under ice-cooling for 15 minutes. After adding ethyl acetate, the mixture was washed in turn with water, dilute hydrochloric acid, an aqueous solution of sodium hydrogencarbonate and saturated brine, dried over magnesium sulfate, and the solvent was distilled off under reduced pressure. To a solution of the residue in dimethylsulfoxide (21 ml) was added a solution of triethylamine (8.6 ml)/formic acid (5.4 ml), and the mixture was stirred at 70° C. for 41 hours. After adding ethyl acetate, the mixture was washed with water and saturated brine in turn, dried over magnesium sulfate, and the solvent was distilled off under reduced pressure. p-Toluenesulfonic acid monohydrate (40 mg) was added to a solution of the residue in methanol (50 ml), the mixture was stirred at 60° C. for one hour, and the solvent was distilled off under reduced pressure. To the solution was added ethyl acetate, the mixture was washed with an aqueous solution of sodium hydrogencarbonate and saturated brine in turn, and dried over magnesium sulfate. The solvent was distilled off under reduced pressure to give 6-(2-(S)-hydroxypropyl)-2,3-dihydro-1,4-benzodioxin-(N-(1-(S )-phenylethyl))-2-(R)-carboxamide (yield=69%, the purity of the optical isomer=92% by HPLC-1 analysis (S/R=92/8, the purity of the material optical isomer used=96%)). Yield was calculated by HPLC-3 analysis.

EXAMPLE 26

To a solution of 6-(2-(R)-hydroxypropyl)-2,3-dihydro-1,4-benzodioxin-( N-(1-(S)-phenylethyl))-2-(R)-carboxamide (7.0 g) in methylene chloride (110 ml) were added 4-dimethylaminopyridine (6.3 g) and p-toluenesulfonyl chloride (7.8 g) at room temperature, and the solution was stirred for 16 hours. To the reaction solution was added chloroform, the mixture was washed in turn with dilute hydrochloric acid, an aqueous solution of sodium hydrogencarbonate and saturated brine, dried over magnesium sulfate, and the solvent was distilled off under reduced pressure. To a solution of the residue in dimethylsulfoxide (21 ml) was added a solution of triethylamine(8.6 ml)/formic acid (5.4 ml), and the mixture was stirred at 70° C. for 9 hours. To the solution was added ethyl acetate, and the mixture was washed with water and saturated brine in turn, dried over magnesium sulfate, and the solvent was distilled off under reduced pressure. To a solution of the residue in methanol (50 ml) was added p-toluenesulfonic acid monohydrate (340 mg), the solution was stirred at 60° C. for one hour, and the solvent was distilled off under reduced pressure. To the solution was added ethyl acetate, the mixture was washed with an aqueous solution of sodium hydrogencarbonate and saturated brine in turn, and dried over magnesium sulfate. The solvent was distilled off under reduced pressure to give 6-(2-(S)-hydroxypropyl)-2,3-dihydro-1,4-benzodioxin-( N-(1-(s)-phenylethyl))-2-(R)-carboxamide (yield=70%, the purity of the optical isomer=95% by HPLC-1 analysis (S/R=95/5, the purity of the material optical isomer used= 96%)). Yield was calculated by HPLC-3 analysis.

EXAMPLE 27

To a solution of 6-(2-(R)-hydroxypropyl)-2,3-dihydro-1,4-benzodioxin-( N-(1-(S)-phenylethyl))-2-(R)-carboxamide (7.0 g) in methylene chloride (110 ml) were added 4-dimethylaminopyridine (6.3 g) and p-toluenesulfonyl chloride (7.8 g) at room temperature, and the solution was stirred for 16 hours. To the reaction solution was added chloroform, the mixture was washed in turn with dilute hydrochloric acid, an aqueous solution of sodium hydrogencarbonate and saturated brine, dried over magnesium sulfate, and the solvent was distilled off under reduced pressure. To the residue was added a solution of triethylamine(8.6 ml)/formic acid (5.4 ml), and the mixture was stirred at 60° C. for 28 hours. To a solution was added ethyl acetate, and the mixture was washed in turn with water, dilute hydrochloric acid, an aqueous solution of sodium hydrogencarbonate and saturated brine, dried over magnesium sulfate, and the solvent was distilled off under reduced pressure. To a solution of the residue in methanol (50 ml) was added p-toluenesulfonic acid monohydrate (350 mg), the solution was stirred at 60° C. for one hour, and the solvent was distilled off under reduced pressure. To the residue was added ethyl acetate, the mixture was washed with an aqueous solution of sodium hydrogencarbonate and saturated brine in turn, dried over magnesium sulfate, and the solvent was distilled off under reduced pressure. The residue was crystallized from xylene/hexane to give 6-(2-(S)-hydroxypropyl)-2,3-dihydro-1,4-benzodioxin-(N-(1-(S)-phenylethyl) )-2-(R)-carboxamide (5.6 g, yield=80%). HPLC-1 analysis of the optical isomer showed 92.5% purity (S/R=92.5/7.5, the purity of the material optical isomer used=96%)).

REFERENCE EXAMPLE 1 a) A suspension of 6-formyl-2,3-dihydro-1,4-benzodioxin-( N-(1-(S)-phenylethyl))-2-(R)-carboxamide (208.15 g) and cyclohexylamine (84 ml) in benzene was heated under reflux using Dean-Stark apparatus for 1.5 hours. The reaction solution was distilled off under reduced pressure, nitroethane (144 ml) and acetic acid (750 ml) were added to the residue, and the mixture was stirred at 110–120° C. for 2 hours. The reaction solution was distilled off under reduced pressure, ethyl acetate was added to the residue, and the mixture was washed with water three times. The solution was washed with an aqueous solution of sodium hydrogencarbonate and saturated brine in turn, dried over magnesium sulfate, and filtered through Celite. The solvent was distilled off under reduced pressure to give a yellow solid (310 g).

$^1$H-NMR (CDCl$_3$) δ: 1.57 (d, 3H, 8H), 2.54 (s, 3H), 4.19 (dd, 1H, J=8Hz, 12Hz), 4.57 (dd, 1H, J=3Hz, 12Hz), 4.77 (dd, 1H, J=3Hz, 8Hz), 5.19 (quint, 1H, J=7Hz), 6.75 (d, 1H, J=8Hz), 7.00–7.05 (m, 3H), 7.17–7.32 (m, 5H), 7.99 (s, 1H)

b) A suspension of the crude product (310 g) obtained in a) above in ethanol (680 ml) was heated while stirring. After dissolving, iron powder (186 g) and water (230 ml) were added. The solution was heated at 70° C., and acetic acid (855 ml) was added dropwise over one hour. After completion of the dropwise addition, the solution was further heated while stirring for one hour. The solution was cooled to room temperature, methanol (400 ml), 5% aqueous hydrochloric acid (375 ml) and Celite (18 g) were added thereto, and the mixture was stirred for one hour. After filtration through Celite, the solvent was distilled off under reduced pressure. To the residue was added ethyl acetate, and the solution was washed with 10% hydrochloric acid, water, a saturated solution of sodium hydrogencarbonate and saturated brine. After drying over magnesium sulfate, the solvent was distilled off under reduced pressure. The residue was crystallized from ethanol/hexane to give 6-(2-oxopropyl)-2,3-dihydro-1,4-benzodioxin-( N-(1-(s)-phenylethyl))-2-(R)-carboxamide (177 g, yield=78%).

$^1$H-NMR (CDCl$_3$) δ: 1.55 (d, 1H, J=7Hz), 2.24 (s, 3H), 3.55 (s, 2H), 4.13 (dd, 1H, J=8Hz, 12Hz), 4.52 (dd, 1H, J=3Hz, 12Hz), 4.69 (dd, 1H, J=3Hz, 8Hz), 5.18 (quint, 1H, J=8Hz), 6.71 (dd, 1H, J=2Hz, 8Hz), 6.75 (d, 1H, J=2Hz), 6.78 (d, 1H, J=8Hz), 6.92 (d, 1H, J=8Hz), 7.18–7.32 (m, 5H)

REFERENCE EXAMPLE 2

To a suspension of 6-(2-oxopropyl)-2,3-dihydro-1,4-benzodioxin-( N-(1-(S)-phenylethyl))-2-(R)-carboxamide (207 g) in methanol (1000 ml) was slowly added sodium borohydride (23 g) under ice-cooling. After 30 minutes, the solution reaction was allowed to stand at room temperature, and stirred for 2 hours. To the reaction solution was added acetone, which was then distilled off under reduced pressure. To the residue was added chloroform, washed in turn with 1N aqueous solution of hydrochloric acid, a saturated solution of sodium hydrogencarbonate and saturated brine. After drying over magnesium sulfate, the solution was filtered through Celite, and the solvent was distilled off under reduced pressure to give 6-(2-hydroxypropyl)-2,3-dihydro-1,4-benzodioxin-( N-(1-(S)-phenylethyl))-2-(R)-carboxamide (207.45 g, quantitatively).

$^1$H-NMR (CDCl$_3$) δ: 1.25 (d, 3H, J=7Hz), 1.57 (d, 1H, J=7Hz), 2.59(dd, 1H, J=8Hz, 14Hz), 2.69 (dd, 1H, J=6Hz, 14Hz), 3.95 (sext, 1H, J=7Hz), 4.14 (dd, 1H, J=8Hz, 12Hz), 4.52 (dd, 1H, J=3Hz, 12Hz), 4.68 (dd, 1H, J=3Hz, 8Hz), 5.17 (quint, 1H, J=7Hz), 6.72 (dd, 1H, J=2Hz, 8Hz), 6.76 (d, 1H, J=2Hz), 6.88 (d, 1H, qqw2J=8Hz), 6.90 (d, 1H, J=8Hz), 7.18–7.32 (m, 5H)

What is claimed is:

1. A process for preparing a compound of formula (7')

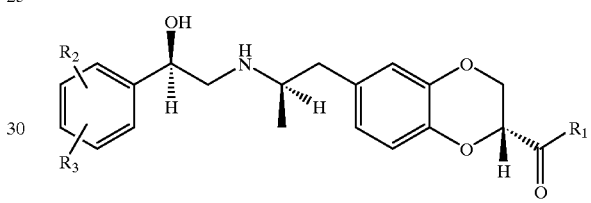

(7')

wherein R, R$_2$ and R$_3$ are as defined below and R$_1$ is hydroxy or (C$_1$–C$_4$)alkoxy, which comprises hydrolyzing a compound of formula (7)

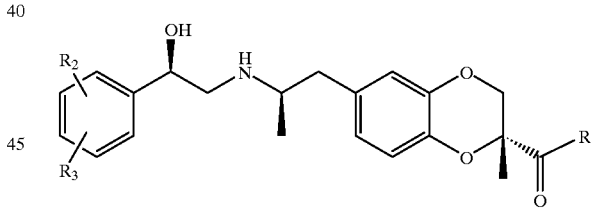

(7)

wherein R is (R)-1-phenylethylamino or (S)-1-phenylethylamino and R$_2$ and R$_3$ may be the same or different, and each is hydrogen, halogen, (C$_1$–C$_6$)alkyl, trifluoromethyl, (C$_1$–C$_6$)alkoxy, aryl, aryloxy or aryl(C$_1$–C$_6$) alkyloxy, the aryl, aryloxy or aryl(C$_1$–C$_6$)alkyloxy being optionally substituted by one or two halogen atoms or R$_2$ and R$_3$ together may form —OCH$_2$O—, and optionally esterifying.

* * * * *